United States Patent [19]
Deigin et al.

[11] Patent Number: 6,159,940
[45] Date of Patent: Dec. 12, 2000

[54] METHOD FOR MODULATING HEMOPOIESIS

[75] Inventors: Vladislav I. Deigin, North York, Canada; Andrei M. Korotkov, Moscow, Russian Federation

[73] Assignee: Immunotech Developments Inc., Toronto, Canada

[21] Appl. No.: 09/340,029

[22] Filed: Jun. 28, 1999

Related U.S. Application Data

[63] Continuation-in-part of application No. 08/894,963, filed as application No. PCT/RU96/00046, Feb. 28, 1996, Pat. No. 6,051,683.

[51] Int. Cl.⁷ .......................... A61K 38/00; A61K 38/05; A61K 38/06
[52] U.S. Cl. ................ 514/18; 514/19; 530/331; 530/330
[58] Field of Search ................ 514/18, 19; 530/330, 530/331

[56] References Cited

U.S. PATENT DOCUMENTS

| | | | |
|---|---|---|---|
| 4,190,646 | 2/1980 | Goldstein et al. | 424/177 |
| 4,603,121 | 7/1986 | Hansen, Jr. et al. | 514/18 |
| 4,619,916 | 10/1986 | Di Stazio et al. | 514/18 |
| 4,699,897 | 10/1987 | Jones et al. | 514/4 |
| 4,699,898 | 10/1987 | Gottlieb | 514/18 |
| 4,751,216 | 6/1988 | Gottlieb | 514/18 |
| 4,910,296 | 3/1990 | Birr et al. | 530/324 |
| 5,008,246 | 4/1991 | Schön et al. | 514/18 |
| 5,013,723 | 5/1991 | Sisto et al. | 514/19 |
| 5,070,076 | 12/1991 | Morozov et al. | 514/21 |
| 5,538,951 | 7/1996 | Morozov et al. | 514/19 |
| 5,736,519 | 4/1998 | Deigin et al. | 514/18 |
| 6,051,683 | 4/2000 | Deigin | 514/19 |

FOREIGN PATENT DOCUMENTS

| | | |
|---|---|---|
| 29308 | 1/1989 | Australia . |
| 0148133 | 7/1985 | European Pat. Off. . |
| 136720 | 9/1989 | European Pat. Off. . |
| 137904 | 2/1990 | European Pat. Off. . |
| 4014230 | 11/1990 | Germany . |
| 654841 | 3/1986 | Switzerland . |
| 1277903 | 12/1986 | U.S.S.R. . |
| 2109796 | 6/1983 | United Kingdom . |
| WO 89/06134 | 7/1989 | WIPO . |
| WO 92/09628 | 6/1992 | WIPO . |
| WO 93/08815 | 5/1993 | WIPO . |
| 96/26955 | 9/1996 | WIPO . |
| 96/40740 | 12/1996 | WIPO . |

OTHER PUBLICATIONS

Goldstein et al., J. Proc. Natl. Acad. Sci. USA, 74:725, 1977.

*Primary Examiner*—F. T. Moezie
*Attorney, Agent, or Firm*—Bereskin & Parr

[57] ABSTRACT

A peptide of the formula I

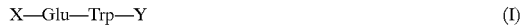

X—Glu—Trp—Y           (I)

wherein X is H or Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, γ-aminobutyric acid, ξ-aminocaproic acid, and Y is Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, γ-aminobutyric acid, ξ-aminocaproic acid, —OH, mono- or di-substituted amide ($c_1$–$c_3$) and the uses therefore in modulating the immune system and hemopiesis.

9 Claims, 4 Drawing Sheets

METHOD FOR MODULATING HEMOPOIESIS

This application in a continuation-in-part of U.S. application Ser. No. 08/894,963 filed Sept. 2, 1997 now U.S. Pat. No. 6,051,683, which is a national phase entry of PCT application No. PCT/RU96/00046 filed Feb. 28, 1996, and which are incorporated herein by reference.

FIELD OF THE INVENTION

The invention relates to a biologically active peptide; a novel pharmaceutical composition containing the peptide; a method for preparing the peptide; and uses of the peptide.

BACKGROUND OF THE INVENTION

Extracts from the thymus gland are known as regulators of immune processes. For example, U.S. Pat. No. 5,070,026 to Morozov et al. (corresponding to Swiss patent No. CH 659,586) teaches a thymus gland preparation containing polypeptides of varying composition and their use in stimulating immunological activity and enhancing reparative processes and hemopoiesis. Goldstein et al. (*Proc. Natl. Acad. Sci. U.S.A.*, 74(2):725–729, February 1997) teaches the isolation of thymosin, which comprises various biologically reactive polypeptides isolated from the thymus gland, and its use in enhancing immunological responses. U.S. Pat. No. 4,910,296 to Birr et al. and European Patent application Ser. No. 89/102569 to Lattanzi teach a composition containing human Thymosin Alpha 1 and fragments thereof which have immunoregulatory and immunostimulatory properties.

Thymic extracts consist of complexes of polypeptides. Their production from natural sources is limited by the complexity of the process, the relatively small yields of active substances, and the large variability of the physical, chemical characteristics and biological properties of the products. In addition, unwanted components which are present in natural thymic preparations sometimes cause side effects.

These problems create a demand for the identification and preparation of synthetic peptides. Several peptides with immunoregulatory properties have been synthesized (see, for example, SU 1,582,393; EP 230,052; U.S. Pat. No. 4,190,646; U.S. Pat. No. 5,008,246; and U.S. Pat. No. 5,013,723). Many scientific laboratories have tried to develop methods for preparing synthetic derivatives of natural peptides, which are more active than their natural analogs (see, for example, EP 0,136,720, 1984; EP 0,137,904, 1984).

Australian Patent No. AU-B-29308/89 (corresponding to WO 08906134) teaches the preparation of Glu-Trp and its use for treating immune deficiency conditions. WO 9308815 to Khavinson et al. discloses the peptide Glu-Trp and cyclic monomers and polymers thereof, for use in the treatment of immunosuppression. Semina et al. (*Radiatsionnaya Biologiya Radioekologiya* 33(3), 1993; WO 8906134) have shown that the levorotary (L) enantiomer of the dipeptide H-Glu-Trp-OH acts as an immunostimulant and can induce the proliferation of cells.

However, the known synthetic peptides do not always have the necessary immunoregulatory properties, and effectiveness. Furthermore, many of them are effective only in large doses that can cause side effects.

SUMMARY OF THE INVENTION

The present inventors have synthesized a series of highly active compounds of the general formula X-Glu-Trp-Y, and have found that these peptides have immunoregulatory properties that are superior to the peptides of the prior art. The identified peptides have the ability to effectively modulate the immune system of humans and animals, in relatively low doses, and with little or no side effects. The present inventors have further found that these peptides have hemopoietic properties. The peptides are prepared using a method which provides high yields with simple and efficient steps.

Broadly stated, the present invention relates to a peptide of the formula I

$$X\text{—Glu—Trp—Y,} \qquad (I)$$

wherein X is H, Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, His, Lys, Arg γ-aminobutyric acid, or ξ-aminocaproic acid; Y is Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, Arg, γ-aminobutyric acid, ξ-aminocaproic acid, —OH, $NH_2$, $N_2H_3$, or a mono- or di-substituted amide ($C_1$–$C_3$); with the proviso that when X is H, Y is not —OH.

Preferred peptides of the invention have the sequence H-Ile-Glu-Trp-OH, His-Glu-Trp-OH, H-Glu-Trp-$NH_2$, H-Glu-Trp-Arg, Lys-Glu-Trp-OH, Arg-Glu-Trp-OH, H-Glu-Trp-Tyr, Lys-Glu-Trp-Tyr, H-Glu-Trp-$N_2H_3$, H-Glu-Trp-Gly, or Val-Glu-Trp-OH. In a further preferred embodiment, the peptide of the present invention is H-Ile-Glu-Trp-OH ["Neogen"].

The invention also relates to analogs and derivatives of the peptides of the invention and cyclized peptides. The term "peptide" or "peptides" used herein includes these analogs, derivatives and cyclized peptides.

The present invention further relates to a process for preparing a peptide of the formula I.

In another embodiment, the invention provides a method of regulating the immune system and/or hemopoiesis in an animal comprising administering to the animal an effective amount of the peptide of the invention. In one embodiment, the invention provides a method of stimulating the immune system of an animal. In yet another embodiment, the invention provides a method of restoring hemopoiesis in an animal with impaired hemopoiesis.

In yet another embodiment the invention provides a method of treating hemopoietic disorders, for example, without limitation to immune cytopenia, multiple myeloma, chronic lymphoid leukosis, lymphocytic lymphomas, lymphosarcomas and in particular to β-cellular lymphoid leukosis.

In another embodiment the invention provides a method for treating immune and/or hemopoietic disorders such as cancer in an animal comprising administering to the animal a peptide of the invention, preferably in combination with cytostatic treatment such as a cytostatic agent. Most preferably the peptide is H-Ile-Glu-Trp-OH and the cytostatic treatment comprises the administration of either oxyurea or heat.

Preferably the peptide is administered in an amount of 0.001 to 0.1 mg/kg by weight of the animal.

The invention still further relates to a pharmaceutical composition comprising one or more peptides of the invention and a pharmaceutically acceptable carrier, the use of a peptide of the Formula I to regulate the immune system, and a method of regulating the immune system.

Other, features and advantages of the present invention will become apparent from the following detailed description. It should be understood, however, that the detailed description and the specific examples, while indicating preferred embodiments of the invention are given by way of illustration only, since various changes and modifications within the spirit and scope of the invention will become apparent to those skilled in the art from this detailed description.

DETAILED DESCRIPTION OF THE INVENTION

I. Peptides of the Invention

Figure 1:
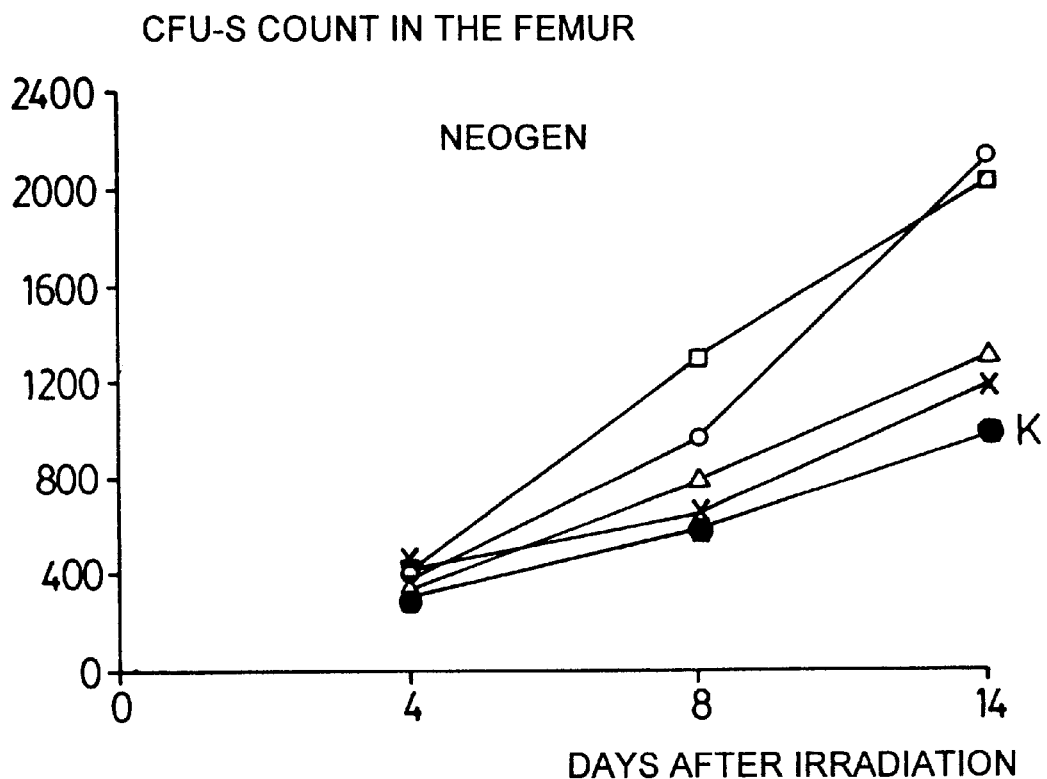
FIG. 1 is a graph which illustrates the effect of intramuscular injections of H-Ile-Glu-Trp-OH on regeneration of the CFU-S population in irradiated mice (4 Gy) wherein the injections are first administered immediately after irradiation.

As mentioned previously, the present invention relates to a peptide of the formula I:

X—Glu—Trp—Y, (I)

wherein X is H, Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, His, Lys, Arg γ-aminobutyric acid, or ξ-aminocaproic acid; Y is Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, Arg, γ-aminobutyric acid, ξ-aminocaproic acid, —OH, NH$_2$, N$_2$H$_3$, or a mono- or di-substituted amide (C$_1$-C$_3$); with the proviso that when X is H, Y is not —OH.

Preferred peptides of the invention have the sequence H-Ile-Glu-Trp-OH, His-Glu-Trp-OH, H-Glu-Trp-NH$_2$, H-Glu-Trp-Arg, Lys-Glu-Trp-OH, Arg-Glu-Trp-OH, H-Glu-Trp-Tyr, Lys-Glu-Trp-Tyr, H-Glu-Trp-N$_2$H$_3$, H-Glu-Trp-Gly, or Val-Glu-Trp-OH. In a further preferred embodiment, the peptide of the present invention is H-Ile-Glu-Trp-OH.

The following standard abbreviations for the amino acid residues are used throughout the specification: Abu—γ-aminobutyric acid; Aca—ξ-aminocaproic acid; Ala—alanine; Cys—cysteine; Asp—aspartic acid; Glu—glutamic acid; Phe—phenylalanine; Gly—glycine; His—histidine; Ile—isoleucine; Lys—lysine; Leu—leucine; Met—methionine; Asn—asparagine; Pro—proline; Gln—glutamine; Arg—arginine; Ser—serine; Thr—threonine; Val—valine; Trp—tryptophan; Tyr—tyrosine; and Orn—ornithine.

The term "analog" includes any peptide having an amino acid residue sequence substantially identical to the sequence of the peptides described herein in which one or more residues have been conservatively substituted with a functionally similar residue and which displays the ability to mimic a peptide of the invention. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

The term derivatives as used herein refers to chemical derivatives of a subject peptide having one or more residues chemically derivatized by reaction of a functional side group. Thus, a "derivative" is a peptide that is derived from a peptide identified herein by one or more chemical steps. Such derivatized molecules include, for example, those molecules in which free amino groups have been derivatized to form amine hydrochlorides, P-toluene sulfoamides, benzoxycarboamides, T-butyloxycarboamides, thiourethane-type derivatives, trifluoroacetylamides, chloroaceamides, or formamides. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized for form N-imbenzylhistidine. Also included as derivatives are those peptides which contain one or more naturally occurring amino acids derivatives of the 20 standard amino acids. For example, 4-hydroxyproline may be substituted for proline; 5-hydroxylysine may be substituted for lysine; 3-methylhistidine may be substituted for histidine; homoserine may be substituted for serine, and ornithine may be substituted for lysine.

The invention further includes cyclic derivatives of the peptides of the invention. Cyclization allows the peptide to assume a more favourable conformation. Cyclization of the peptides may be achieved using techniques known in the art. In particular, disulphide bonds may be formed between two appropriately spaced components having free sulfhydryl groups. The bonds may be formed between side chains of amino acids, non-amino acid components, or a combination of the two.

As will be discussed in more detail below, the invention also includes a peptide of the invention conjugated with a selected protein, or a selectable marker to produce fusion proteins.

Peptides of the invention may be converted into pharmaceutical salts by reacting with inorganic acids including, without limitation, hydrochloric acid, sulfuric acid, hydrobromic acid, phosphoric acid, or organic acids including formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

The peptides of the invention may be prepared by chemical synthesis using techniques known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

According to an embodiment of the present invention, the peptide of the formula (I) is synthesized by step-by-step building of the peptide chain beginning with the C-terminal amino acid. The process involves maximum blocking of functional groups, starting from an amino acid alkyl ester, using the method of active esters and the method of mixing anhydrides, preferably using a t-butyloxycarbonyl group as the amino protecting group.

In a preferred embodiment, the method involves the blocking of the amino, carboxyl and other reactive side groups of the amino acid(s) which are not to react during the synthesis. Suitable blocking agents would be known to a person skilled in the art. For example, a suitable carboxy blocking agent would include, without limitation, ethyl, nitrobenzyl, and t-butyl. A suitable amino blocking agent would include, without limitation, carbobenzoxy, tosyl, trifluoracetyl and preferably t-butyloxycarbonyl (Boc). The amino acids are then coupled and the blocking agents subsequently removed. The peptide can optionally be further purified using reverse phase chromatography, preferably in acetonitrile/0.1% trifluoracetic acid.

Most preferably, the C-terminal amino acid is blocked at its amino terminal end, preferably with t-butyloxycarbonyl and coupled to another molecule, such as pentafluorophenol, to form an amino acid alkyl-ester. This occurs by chilling the mixture of the protected amino acid and pentaflorophenol in ethylacetate to about −5 degrees celsius and adding N,N-dicyclohexylcarbodiimide. The mixture is then stirred at room temperature for three hours, the forming N,N-dicyclohexylurea removed by filtration, the remains crystallized in ethylacetate-hexane and the residue filtered out. The amino protected alkyl-ester amino acid is then coupled to another amino acid or peptide, such as Glu-Trp, in the pressence of dimethylformamide, to give an amino protected peptide, such as Boc-Ile-Glu-Trp-OH. The blocking agent, Boc, is then removed using conventional methods known in the art and the peptide purified using reverse phase HPLC chromatography.

The peptide prepared using this process is a yellowish grey or white powder, soluble in water, substantially insoluble in alcohol and substantially insoluble in chloroform. It has a UV spectrum in the range of 250–300 nm with a maximum at 280±2 nm.

This process provides high yields of the product with a minimum number of steps, and maximum efficiency and simplicity.

N-terminal or C-terminal fusion proteins comprising a peptide of the invention conjugated with other molecules such as proteins or selectable markers may be prepared by fusing, through recombinant techniques, the N-terminal or C-terminal of the peptide, and the sequence of a selected protein or selectable marker with a desired biological function. The resulting fusion proteins contain the peptide fused to the selected protein or marker protein as described herein.

In the alternative, the peptides of the invention may be prepared using recombinant techniques. Nucleic acid molecules which encode a peptide of the invention may be incorporated in a known manner into an expression vector which ensures good expression of the peptide. Suitable expression vectors include but are not limited to cosmids, plasmids, or modified viruses so long as the vector is compatible with the host cell used. The expression vectors contain a nucleic acid molecule encoding a peptide of the invention and regulatory sequences necessary for the transcription and translation of the inserted protein-sequence. Regulatory sequences may be obtained from a variety of sources, such as bacterial, fungal, viral, mammalian, or insect genes (See the regulatory sequences described in Goeddel, Gene Expression Technology: Methods in Enzymology 185, Academic Press, San Diego, Calif. (1990)). The selection of regulatory sequences is dependent on the host cell chosen, and may be readily accomplished by one of ordinary skill in the art. Sequences, including an origin of replication, additional DNA restriction sites, enhancers, and sequences conferring educability of transcription may also be incorporated into the expression vector.

A selectable marker gene which facilitates the selection of transformed or transfected host cells may also be included in the recombinant expression vector. Examples of selectable marker genes are genes encoding proteins such as G418 and hygromycin which confer resistance to certain drugs, β-galactosidase, chloramphenicol acetyltransferase, and firefly luciferase. It will be appreciated that the selectable markers may be introduced on a separate vector from the nucleic acid.

Genes may also be included in the recombinant expression vectors which encode a fusion portion which provides increased expression of the recombinant peptide; increased solubility of the recombinant peptide; and/or aid in the purification of the recombinant peptide by acting as a ligand in affinity purification. In particular, a proteolytic cleavage site may be inserted to allow separation of the recombinant peptide from the fusion portion after purification of the fusion protein.

A recombinant expression vector may be introduced into a host cell to produce a transformant host cell. Transformant host cells include prokaryotic and eukaryotic cells transformed or transfected with a recombinant expression vector of the invention. The terms "transformed with", "transfected with", "transformation" and "transfection" include the introduction of nucleic acid (e.g. a vector) into a host cell by one of many techniques known in the art. Examples of methods for transforming and transfecting host cells may be found in Sambrook et al. (Molecular Cloning: A Laboratory Manual, 2nd Edition, Cold Spring Harbor Laboratory press (1989)), and other laboratory textbooks.

Suitable host cells include prokaryotic and eukaryotic host cells. In particular, the peptides of the invention may be expressed in bacterial cells such as *E. coli*, insect cells (using baculovirus), yeast cells or mammalian cells. Other suitable host cells are described in Goeddel, Gene Expression Technology: Methods in Enzymology 185, Academic Press, San Diego, Calif. (1991).

Monoclonal or polyclonal antibodies specific for the peptides of the invention may be prepared using conventional methods. For example, the preparation of monoclonal antibodies can be carried out as described in Goding, J. W., Monoclonal Antibodies: Principles and Practice, 2nd Ed., Academic Press, London, 1986.

The peptides of the invention may be labelled using conventional methods with various enzymes, fluorescent materials, luminescent materials and radioactive materials. Suitable enzymes, fluorescent materials, luminescent materials, and radioactive material are well known to a person skilled in the art.

III. Uses of the Peptide

The present invention offers peptides that can be used for experimental purposes and in medicine. The peptides and pharmaceutical compositions containing the peptides have significant immunoregulatory effects and accordingly may be used to promote or suppress recognition and destruction of abnormal or mutant cell types or antigens which arise within the body. In vitro, the claimed peptide was found to be $10^3$ times as active as known preparations. The utility of the peptides of the present invention can be seen in more detail with reference to the Examples.

In one aspect, the invention provides a method of modulating the immune system and/or hemopoiesis in an animal comprising administering to the animal an effective amount of the peptide of the invention. In one embodiment, the invention provides a method of stimulating the immune system of an animal. In another embodiment, the invention provides a method of restoring hemopoiesis in an animal with impaired hemopoiesis, for example caused by irradiation or cytostatic agents.

In yet another embodiment the invention provides a method of treating hemopoietic disorders, for example, without limitation to immune cytopenia, multiple myeloma, chronic lymphoid leukosis, lymphocytic lymphomas, lymphosarcomas and in particular β-cellular lymphoid leukosis.

In another embodiment the invention provides a method for treating immune and/or hemopoietic disorders such as cancer in an animal comprising administering to the animal an effective amount of a peptide of the invention, preferably in combination with a cytostatic agent. Most preferably the peptide is H-Ile-Glu-Trp-OH and the cytostatic agent is either oxyurea or hyperthermia.

The peptides may be administered to animals in an effective amount. The term "animal" as used herein refers to any living organism in which an immune or hemopoietic response can be elicited, including without limitation to mammals, such as mice guinea pigs, rats, rabbits and humans. An "effective" amount is defined as an amount of the active ingredient i.e. peptides, effective, at dosages and for periods of time necessary to achieve the desired result. An effective amount of a peptide may vary according to factors such as the disease state, age, sex, and weight of the individual. Dosage regime may be altered to provide the optimum therapeutic response.

The peptides of the invention can be formulated into pharmaceutical compositions for adminstration to subjects in a therapeutically effective amount and in a biologically compatible form suitable for administration in vivo, i.e. a form of the peptides to be administered in which any toxic effects are outweighed by the therapeutic effects.

The peptides may be administered by injection (i.e., subcutaneous, intravenous, intramuscular, intraperitoneal, preferably intramuscular), oral administration, inhalation, transdermal application, topical administration or rectal administration, preferably by injection, transdermal or topical administration. Depending on the route of administration, the peptides in the pharmaceutical compositions may be coated in a material to protect them from the action of certain enzymes. A person skilled in the art would be familiar with the coating which would be suitable for delivery of the peptide to a particular site. Organic substances may also be included in the compositions to prolong the pharmacologic actions of the peptides. Examples of such organic substances include non-antigenic gelatin, carboxymethylcellulose, sulfonate or phosphate ester of alginic acid, dextran, polyethylene glycol and other glycols, phytic acid, polyglutamic acid, and protamine.

The pharmaceutical compositions of the invention can be prepared by per se known methods for the preparation of pharmaceutically acceptable compositions which can be administered to subjects, such that an effective quantity of a peptide is combined in a mixture with a pharmaceutically acceptable vehicle. Examples of pharmaceutically acceptable vehicles are described in Remington's Pharmaceutical Sciences (Remington's Pharmaceutical Sciences, Mack Publishing Company, Easton, Pa., USA 1985).

Compositions for injection include, albeit not exclusively, the peptides in association with one or more pharmaceutically acceptable vehicles or diluents, and contained in buffered solutions with a suitable pH and iso-osmotic with the physiological fluids. Any pharmaceutically suitable diluent can be used in the composition for injections: distilled water, physiological or a salt solution, and/or a buffer solution. The composition for injections may be prepared by conventional volume-weight procedure. A certain amount of the peptide is diluted to the necessary volume with a diluent or solvent. Then the solution is filtered through sterilized filters, bottled or ampouled. The resultant solution is a stable transparent liquid, and does not contain any chemical or other impurities.

In a preferred embodiment of the invention, the pharmaceutical composition generally contains 0.001 or 0.1% (preferably 0.001–0.05%) of one or more of the peptide, of the invention The percentage also depends on the medicinal form-solution or a solid form. A person skilled in the art would appreciate that the treatment regimen may vary according to the condition to be treated and the individual. The preferred dosage of the peptide is 0.001–0.1 mg/kg, and more preferably 0.001–0.01 mg/kg. The petide is preferably administered daily and preferably for a period of 3 to 10 days. The preferred pharmaceutical composition is made by mixing the carrier and the peptide at the temperature of 40°–70° C. The composition is stable in solution for 24 months (2 years) at 70° F. (20° C.) and for 36 months at 4° C.

The composition for injections may contain any pharmaceutically suitable solvent, including distilled water, physiological solution, saline, or buffer solutions. The ratio of the peptide to vehicle is preferably 0.001 to 0.1%.

The solution for injections is made by the conventional volumetric-gravimetric method. The solvent is added to a certain accurately weighed amount of the peptide powder to make the necessary volume. The solution is filtered through a sterilizing filter, bottled or ampouled. The solution is a colorless transparent liquid. It is stable and contains no other impurities.

Solid form preparations for oral administration can be made in the form of tablets, powders, capsules. It may contain a medium for the active substance and other additives, including dyes, aromas, etc. A person skilled in the art would understand that the oral compositions may be coated in a particular material to protect them from the action of certain enzymes. The peptide percentage may be from 0.001% to 0.1% and usually depends on the type of the composition for oral use.

The peptide or pharmaceutical compositions of the invention can be packaged into lyposomes and administered in the form of topical creams or aerosols. Further, the peptide can be administered via active transdermal films or aerosols forms such as nasal sprays.

An acute toxicity study of the peptide was carried out in compliance with methodical recommendations of the Pharmacological Committee of the Russian Federation (RF), "Requirements to Preclinical Study of General Toxic Action of New Pharmacological Substances", M., 1985. According to the results of the study, intraperitoneal injection of a 10,000-fold dose of the peptide did not cause an acute toxic effect.

Thus, the new peptides are nontoxic and have a potent immunoregulatory effect.

The following non-limiting examples are illustrative of the present invention:

EXAMPLE 1

This example outlines the synthesis of one peptide of the invention, H-Ile-Glu-Trp-OH.

1. Preparation of Boc-Ile-OPFP

A mixture of 46.0 g (0.2 M) Boc-Ile-OH and 40.5 g (0.22 M) pentafluorophenol in 100 ml ethyl acetate was cooled to $-5°$ C. To this was added 45.3 g (0.22 M) N,N-dicyclohexyl carbodiimide. The reaction mixture was stirred at room temperature for 3 h. Resulting dicyclohexylurea was removed by filtration. The solvents were subsequently evaporated under vacuum. The remaining residue was crystallized in a mixture of ethyl acetate-hexane. The precipitate was separated by filtration. Yield: 71.3 g (90%).

2. Preparation of Boc-Ile-Glu-Trp-OH 19.8 g (0.05 M) Boc-Ile-OPFP was dissolved in 100 ml dimethyl formamide. To this was added a water solution of 20 g (0.06 M) Glu-Trp and 5.0 g (0.06 M) $NaHCO_3$. The solution was stirred for 20 h at room temperature, then the solvents were removed by evaporation under vacuum. To this was added 200 ml ethyl acetate and 20 ml 2% sulfuric acid solution and mixed. The organic layer was washed with sulfuric acid solution (2×100 ml), with saturated NaCl solution to pH=7, dried over anhydrous sodium sulfate, and the solvent evaporated under vacuum. The residue was crystallized from ethyl acetate-hexane, the precipitate separated by filtration and dried under vacuum. Yield: 20.5 g (75%).

3. Preparation of H-Ile-Glu-Trp-OH 20.5 g Boc-Ile-Glu-Trp-Oh was dissolved in 150 ml formic acid, stirred for 3.5 h at 45° C. The solvent was evaporated under vacuum. 200 ml water was added to the residue and evaporation under vacuum was repeated. 300 ml isopropanol and 200 ml ether was added to the residue and allowed to stand for 10 h. The precipitate was then filtered and dried under vacuum. Yield: 15.3 g (75%).

The peptide was purified using reverse phase HPLC in acetonytrile—0.1% TFA (trifluoroacetic acid). Yield: 13 g (85%).

The resultant peptide has the physical and chemical properties and characteristics as follows:

Primary structure—H-Ile-Glu-Trp-OH

Empirical formula—$C_{24}H_{30}N_4H_4$

Molecular weight—446.5 Da

Appearance—yellowish-white or grey powder

Solubility—readily soluble in water, moderately soluble in alcohol, insoluble in chloroform.

UV—spectrum in the range of 250–300 nm has the maximum at 280±2 nm and a shoulder at 287±2 nm.

EXAMPLE 2

This example sets out physical organic data with respect to various embodiments of the peptides of the present invention.

Table 1 contains $Rf_1$ (in chloroform-methanol-32% acetic acid=60:45:20) and $Rf_2$ (in butanol-pyridine-water-acetic acid=5:5:4:1) values for a number of compounds of the new peptide.

TABLE 1

| PEPTIDE | $Rf_1$ | $Rf_2$ |
|---|---|---|
| Abu-Glu-Trp-OH | 0.40 | 0.56 |
| Aca-Glu-Trp-OH | 0.41 | 0.57 |
| Ala-Glu-Trp-$NH_2$ | 0.40 | 0.51 |
| Arg-Glu-Trp-OH | 0.26 | 0.48 |
| D-Ala-Glu-Trp-OH | 0.37 | 0.55 |
| D-Ile-Glu-Trp-D-Phe | 0.71 | 0.77 |
| D-Ile-Glu-Trp-OH | 0.39 | 0.54 |
| D-Leu-Glu-Trp-$NH_2$ | 0.35 | 0.56 |
| D-Leu-Glu-Trp-OH | 0.37 | 0.57 |
| D-NVal-Glu-Trp-OH | 0.38 | 0.56 |
| D-Phe-Glu-Trp-Ala | 0.69 | 0.76 |
| D-Pro-Glu-Trp-OH | 0.58 | 0.72 |
| D-Trp-Glu-Trp-OH | 0.47 | 0.56 |
| D-Tyr-Glu-Trp-OH | 0.45 | 0.57 |
| D-Val-Glu-Trp-NH2 | 0.43 | 0.53 |
| Gly-Glu-Trp-Gly | 0.44 | 0.49 |
| Gly-Glu-Trp-OH | 0.42 | 0.56 |
| H-Glu-Trp-Abu | 0.49 | 0.54 |
| H-Glu-Trp-Aca | 0.51 | 0.56 |
| H-Glu-Trp-Arg | 0.28 | 0.40 |
| H-Glu-Trp-D-Ala | 0.61 | 0.70 |
| H-Glu-Trp-D-Ile | 0.63 | 0.71 |
| H-Glu-Trp-D-Leu | 0.64 | 0.72 |
| H-Glu-Trp-D-NVal | 0.65 | 0.69 |
| H-Glu-Trp-D-Pro | 0.66 | 0.69 |
| H-Glu-Trp-D-Trp | 0.63 | 0.66 |
| H-Glu-Trp-D-Tyr | 0.61 | 0.66 |
| H-Glu-Trp-D-Val | 0.65 | 0.71 |
| H-Glu-Trp-Ile | 0.64 | 0.68 |
| H-Glu-Trp-Gly | 0.54 | 0.58 |
| H-Glu-Trp-$NH_2$ | 0.42 | 0.55 |
| H-Glu-Trp-$N_2H_3$ | 0.32 | 0.41 |
| H-Glu-Trp-NVal | 0.67 | 0.71 |
| H-Glu-Trp-Trp | 0.64 | 0.67 |

TABLE 1-continued

| PEPTIDE | Rf$_1$ | Rf$_2$ |
|---|---|---|
| H-Glu-Trp-Tyr | 0.62 | 0.66 |
| H-Glu-Trp-Val | 0.66 | 0.71 |
| His-Glu-Trp-OH | 0.31 | 0.58 |
| Ile-Glu-Trp-Phe | 0.71 | 0.78 |
| Ile-Glu-Trp-OH | 0.38 | 0.54 |
| Ile-Glu-Trp-Phe | 0.72 | 0.78 |
| Ile-Glu-Trp-Pro | 0.68 | 0.81 |
| Leu-Glu-Trp-OH | 0.39 | 0.56 |
| Lys-Glu-Trp-OH | 0.30 | 0.51 |
| Lys-Glu-Trp-Tyr | 0.32 | 0.50 |
| NVal-Glu-Trp-OH | 0.37 | 0.55 |
| Phe-Glu-Trp-NH$_2$ | 0.53 | 0.68 |
| Ile-Glu-Trp-Phe | 0.71 | 0.78 |
| Ile-Glu-Trp-OH | 0.38 | 0.54 |
| Ile-Glu-Trp-Phe | 0.72 | 0.78 |
| Ile-Glu-Trp-Pro | 0.68 | 0.81 |
| Leu-Glu-Trp-OH | 0.39 | 0.56 |
| Lys-Glu-Trp-OH | 0.30 | 0.51 |
| Lys-Glu-Trp-Tyr | 0.32 | 0.50 |
| NVal-Glu-Trp-OH | 0.37 | 0.55 |
| Phe-Glu-Trp-NH$_2$ | 0.53 | 0.62 |
| Pro-Glu-Trp-Leu | 0.67 | 0.75 |
| Pro-Glu-Trp-OH | 0.59 | 0.72 |
| Trp-Glu-Trp-OH | 0.48 | 0.59 |
| Tyr-Glu-Trp-OH | 0.46 | 0.58 |
| Val-Glu-Trp-Ala | 0.61 | 0.71 |
| Val-Glu-Trp-NH$_2$ | 0.38 | 0.52 |
| Val-Glu-Trp-OH | 0.36 | 0.51 |
| Val-Glu-Trp-Tyr | 0.59 | 0.61 |

EXAMPLE 3

This example concerns the ability of a peptide of the invention to stimulate lymphocyte production.

The biological action of the novel peptide was studied in guinea pigs in the conventional E-rosette formation test. Table 2 shows comparative data of the effect of thymic preparations and that of a claimed peptide of the present invention on E-rosette formation of lymphocytes in guinea pigs after trypsin treatment.

TABLE 2

| Compound | Untreated Animal | Treated with Trypsin | After treatment with trypsin and compound with concentration mg/ml* | | | | | | |
|---|---|---|---|---|---|---|---|---|---|
| | | | $10^{-6}$ | $10^{-7}$ | $10^{-8}$ | $10^{-9}$ | $10^{-10}$ | $10^{-11}$ | $10^{-12}$ |
| Tymolin | 66.5 | 36.1 | 57.0 | 40.1 | 37.0 | 35.3 | 37.4 | 36.5 | 34.7 |
| Tymozine Fraction 5 | 66.5 | 36.1 | 60.3 | 35.4 | 33.4 | 39.5 | 39.1 | 33.7 | 35.8 |
| Ile-Glu-Trp | 66.5 | 36.1 | 61.4 | 63.9 | 64.8 | 60.2 | 37.5 | 40.0 | 34.3 |

*Each concentration was tested on 5 animals. The positive growth differs in relation to the control group; E-POK is 50% or higher.

As can be seen from Table 2, it was established that in vitro use of the said peptide is $10^3$ times more active than other known compounds.

EXAMPLE 4

This example illustrates the immunomodulating properties of the peptide. The immumostimulating effect of H-Ile-Glu-Trp-OH was tested in intact animals and with secondary immunodeficiencies, specifically irradiation-induced ones.

Females and male (CBA×C57BL)F1 mice, aged about 2.5 months weighing about 20 g, were irradiated with gamma-rays using a "Luch-1" apparatus. Immunological activity was assessed according to Jerne (Antibody Forming Cells count—AFC). T-cell count in spleen was determined by the method of spontaneous rosette formation with sheep erythrocytes (E-FRC). The peptide was injected intramuscularly.

Mice were irradiated in a dose of 2 Gy, the peptide was injected in the dose of 10 μg/kg according to the following scheme (to determine T-cell count by the method of spontaneous rosette formation): 1 time—an hour after the irradiation; 2 times—an hour, and a day after irradiation; 3 times—an hour, a day, and two days after the irradiation; 4 times—an hour, a day, two days and three days after the irradiation. The intact mice recieved the peptide 3 or 4 times. The control group (2 Gy) recieved injections of physiological solution according to the same schedule. On completion of the treatment course, 10 mice from each group were immunized with sheep erythrocytes (SE) and 4–5 days later AFC counts were determined in their spleens. The rest of the mice were used to find T-cell count by the method of spontaneous rosette formation. The state of the organs of immune system (spleen and thymus) in mice with radiation immunodeficiency against the background of H-Ile-Glu-Trp-OH treatment was also listed by nucleated cell counts in thymus and spleen per mg of organ weight. The results are shown in Tables 3 and 4. AFC/mg Spleen weight is presented as an average of two experiments.

TABLE 3

| Group | AFC/mg Spleen | T-Cell Count, $10^3$/mg Spleen | |
|---|---|---|---|
| | | 1 | 2 |
| Control | 168.0 ± 10.0* | 35.1 ± 2.1 | 15.8 ± 1.2** |
| Irradiation 2 Gy | 81.1 ± 13.1*** | 22.2 ± 2.9## | 6.3 ± 3.2# |
| 2 Gy + Peptide 1 Injection | — | 34.5 ± 1.7## | — |
| 2 Gy + Peptide 2 Injection | — | 35.6 ± 1.8## | — |

TABLE 3-continued

| Group | AFC/mg Spleen | T-Cell Count, $10^3$/mg Spleen | |
|---|---|---|---|
| | | 1 | 2 |
| 2 Gy + Peptide 3 Injection | 152.4 ± 4.1*** | 45.3 ± 3.4## | 23.2 ± 3.7# |
| 2 Gy + Peptide 4 Injection | 158.1 ± 7.1*** | 48.4 ± 2.5## | 13.0 ± 0.8# |

TABLE 3-continued

| | | T-Cell Count, $10^3$/mg Spleen | |
|---|---|---|---|
| Group | AFC/mg Spleen | 1 | 2 |
| Peptide 3 Injections | 621.1 ± 14.2* | | 12.7 ± 1.5 |
| Peptide 4 Injections | 676.1 ± 47.5* | | 18.7 ± 5.8** |

*, , *, ##, #- P < 0.05

TABLE 4

| | Karyocyte Count, $10^3$/mg | |
|---|---|---|
| Group | Spleen | Thymus |
| Control | 1100 ± 90 | 1850 ± 260 |
| Irradiation 2 Gy | 880 ± 50** | 1820 ± 250 |
| 2 Gy + Peptide 1 Injection | 1120 ± 73* | 1860 ± 200 |
| 2 Gy + Peptide 2 Injection | 890 ± 80 | 1840 ± 380 |
| 2 Gy + Peptide 3 Injection | 980 ± 80 | 2590 ± 400 |
| 2 Gy + Peptide 4 Injection | 1160 ± 100* | 2480 ± 280 |

*P < 0.05
**- Significance was calculated relative to this group.

As data in Table 4 show, the peptide injections to irradiated mice (one and four injections) brought about a trustworthy increase in the karyocyte count in spleen per mg of organ weight and, a certain growth of the karyocyte count in thymus (3 and 4 injections). The data in Table 3 show that the number of antibody forming cells practically doubled in irradiated mice injected with the peptide (3 and 4 injections). T-cell count in spleen grew in all mice who received the peptide injections, especially three or four injections.

H-Ile-Glu-Trp-OH thus has a pronounced immunostimulating effect under radiation immunodeficiencies, and it is most effective when injected 3–4 times (Tables 3, 4).

The immunostimulating effect of the peptide is observed not only in irradiated mice. When inducing the humoral response to SE in intact mice, AFC increased 5 times, the T-cell count being the same as it was [Table 3]. Consequently, the peptide had a pronounced immunomodulating effect when injected both to intact and irradiated mice.

EXAMPLE 5

Radiotherapeutic properties of the peptide H-Ile-Glu-Trp-OH and its effect on the population of hemopoietic progenitors was studied. This example demonstrated the use of the peptide to substitute accessory T-cells in regulation of hemopoiesis.

(CBA×C57BL)F1 female mice (n=2500), 2-months old, weighing about 20 g, were used in the experiment.

As is known, there is a close relationship between T-cells and hemopoietic progenitors. It was shown that, along with colony-forming units of spleen (CFU-S), thymocytes participate in colony formation of spleens of irradiated mice by controlling proliferation of the hemopoietic progenitor cells. The fact was established in a test system, which allowed a selective removal of accessory T-cells from bone marrow with the help of rabbit antimouse brain antiserum (RAMBS) and their substitution with other factors. Aliquots (0.1 ml) of bone marrow suspension ($2 \times 10^7$ cells), RAMBS, and medium 199 were mixed and incubated for 1 hour at 37° C. Then the cells were washed with centrifuging, resuspended and injected to lethally irradiated mice. Spleen colony counts were notably lower as compared to control. The colony formation was restored by injecting the mice with additional thymocytes, along with RAMBS-treated bone marrow cells, which proved the participation of T-cells in colony formation.

According to the aforesaid scheme, instead of thymocytes mice received the peptide, H-Ile-Glu-Trp-OH injections 30 minutes before the injections of RAMBS-treated bone marrow suspension. The results are presented in Table 5.

TABLE 5

| RAMBS | Preparation | The Number of Mice | Average Colony Count |
|---|---|---|---|
| − | − | 19 | 10,7 ± 0,7 |
| + | − | 23 | 2,3 ± 0,5 |
| + | thymocytes | 22 | 6,0 ± 0,6 |
| + | the peptide | 20 | 6,3 ± 0,4 |

The peptide was shown to increase colony yields considerably (2–3 times as compared to RAMBS-treated bone marrow), and acted practically at the same level as thymocytes. The same experiment was conducted using the peptide H-Glu-Trp-OH ("Thymogen") instead of H-Ile-Glu-Trp-OH. This resulted in an average colony count of 2.9+/− 0.3. Thus Thymogen does not posess such activity.

EXAMPLE 6

The next example concerns the effect of a peptide of the invention on hemopoiesis after exposure to ionising radiation. The present inventors studied the ability of a peptide of the invention to weaken the harmful effects of ionising radiation.

For this purpose, known methods using exogenous spleen colonies were applied. A suspension of intact marrow cells was irradiated in the dose of 1 Gy. Different doses of the peptide were injected intravenously (i.v.), intraperitoneally (i.p.), or intramuscularly (i.m.) to lethally irradiated recipients an hour after the injections of irradiated bone marrow. Colonies were counted on day 9. 350 mice were used as test animals. The data for each group are the average of three tests.

The data obtained is contained in Table 6 and shows that the peptide can reduce the detrimental effect of radiation on hemopoietic progenitor cells, i.e. the peptide is not only an immunostimulator but has also a definite effect on the initial stages of hemopoiesis.

TABLE 6

| Irradiated Dose | Drug Dose mcg/Kg | i.v. | i.p. | i.m. | Colony Count |
|---|---|---|---|---|---|
| − | − | − | − | − | 10.6 ± 0.4 |
| 1 Gy | − | − | − | − | 3.4 ± 0.5** |
| 1 Gy | 2.5 | + | − | − | 6.0 ± 0.7* |
| 1 Gy | 10 | + | − | − | 8.7 ± 0.4* |
| 1 Gy | 25 | + | − | − | 7.6 ± 0.4* |
| 1 Gy | 50 | + | − | − | 7.1 ± 0.5* |
| 1 Gy | 100 | + | − | − | 6.0 ± 0.5* |
| 1 Gy | 200 | + | − | − | 5.3 ± 0.7* |
| 1 Gy | 500 | + | − | − | 4.2 ± 0.3 |
| 1 Gy | 10 | − | + | − | 8.2 ± 0.7* |
| 1 Gy | 10 | − | − | + | 10.6 ± 0.8* |

TABLE 6-continued

| Irradiated Dose | Drug Dose mcg/Kg | i.v. | i.p. | i.m. | Colony Count |
|---|---|---|---|---|---|
| 3 Gy | – | – | – | – | 0.8 ± 0.2** |
| 3 Gy | 10 | + | – | – | 2.3 ± 0.3* |

From the data of Table 6, it can be seen that IM administration of the peptide was more effective in reconstituting CFU-S colonies than IV or IP administration. A further study of the effect of the peptide, using different methods of administration, on the dynamics of reconstitution of CFU-S, Nucleated blood Cells (NC) in the femoral bone marrow and peritheric blood (mm) of irradiated mice (4 Gy) was conducted.

Donor mice were irradiated with γ-rays in the dose of 4 Gy. Then they received the petide i.v. or i.m. 1, 2, 3, or 4 times, once a day, starting from the 1 first hour of the 3rd day after the irradiation (10 μg/kg per injection). The mice were observed for 14–16 days. At different intervals after the irradiation 10 mice were taken from each group to determine CFU-S in the bone marrow. The mice were killed, cell suspensions were prepared from the bone marrow and injected to lethally irradiated recipients. NC were counted in the femoral bone marrow and peritheric blood, and the lymphocyte percentage was found.

Test animals were 1110 mice.

The study revealed that i.v. injection of H-Ile-Glu-Trp-OH 1, 3, or 4 times had helped better reconstitution of the CFU-S pool by day 14 only. While IM administration of the drug (especially 1, 2, 3 times) positively influenced the reconstitution of the CFU-S pool earlier, beginning from day 8 after the irradiation, but it had no effect on the NC content in the bone marrow, which points to an increase, as compared to control, of the hemopoietic progenitor percentage as a result of the H-Ile-Glu-Trp-OH treatment of irradiated mice. Each group consisted of 10 mice.

EXAMPLE 7

The example illustrates the ability of the peptide to eliminate the cytostatic effect of irradiation (in the dose of 4 Gy) on stem and mature cells of the hemopoietic system in the test of regeneration of the karyocyte counts and CFU-S population in femoral bone marrow and nucleated blood cells (1 mm$^3$).

Irradiated mice (4 Gy) received intramuscular injections of the peptide in the dose of 10 μg/kg according to 2 schemes.

a) Scheme 1: mice received the peptide immediately after irradiation, daily. The mice were divided into groups: a control group—irradiated mice (4 Gy), and test groups—irradiated mice (4 Gy) received the peptide 1, 2, 3, and 4 times daily. Blood samples were taken four hours after the last peptide injection and on the 7th, 10th, and 16th day after the irradiation. Determined were total count of nucleated blood cells (NC) and lymphocyte percentage of them; nucleated cells and the CFU-S population in femoral bone marrow were counted on the 4th, 8th, and the 14th day. The results are presented in Tables 7, 8 and FIG. 1.

TABLE 7

| | Karyocyte Count in blood × 10$^3$/1mm$^3$ on | | | |
|---|---|---|---|---|
| Group | Day 4 | Day 7 | Day 10 | Day 16 |
| Control (4 Gy) | 1.33 ± 0.2 | 5.30 ± 0.9 | 6.00 ± 0.1 | 3.67 ± 0.7* |
| Peptide 1 Time | 0.80 ± 0.5 | 3.53 ± 0.5 | 4.30 ± 0.3 | 4.49 ± 0.8 |
| Peptide 2 Times | 1.30 ± 0.2 | 3.64 ± 0.6 | 6.42 ± 0.7 | 5.96 ± 1.0 |
| Peptide 3 Times | 1.19 ± 0.1 | 5.58 ± 0.7 | 4.18 ± 0.8 | 6.32 ± 0.7* |
| Peptide 4 Times | 1.64 ± 0.2 | 4.14 ± 0.8 | 4.90 ± 0.7 | 7.32 ± 1.0* |
| Intact: NC-6900 ± 25 | Lymphocytes: 4533 ± 213.2 (65.7 ± 3.3) | | | |

*p < 0.05
Survival - 100%

TABLE 8

| | Lymphocytes, % (absolute) in blood on | | | |
|---|---|---|---|---|
| Group | Day 4 | Day 7 | Day 10 | Day 16 |
| Control | 20.0 ± 1.2 (266) | 21.4 ± 1.9 (1130) | 18.8 ± 1.2 (1080) | 29.6 ± 3.2 (1064) |
| Peptide 1 Time | 29.0 ± 2.5 (232) | 38.8 ± 3.1 (1365) | 26.3 ± 2.9 (1118) | 53.6 ± 6.0 (2412) |
| Peptide 2 Times | 36.0 ± 1.7 (468) | 34.8 ± 2.1 (1260) | 25.5 ± 2.7 (1664) | 44.8 ± 6.2 (2682) |
| Peptide 3 Times | 36.0 ± 1.3 (432) | 27.1 ± 1.9 (1512) | 29.5 ± 3.6 (1233) | 44.8 ± 4.80* (2853) |
| Peptide 4 Times | 39.0 ± 2.9 (639) | 25.6 ± 3.7 (1025) | 30.7 ± 6.5 (1475) | 38.5 ± 1.40 (2847) |

According to the data in Table 7, up to the 16th day after the irradiation, in none of the test groups did the karyocyte count in blood exceed the control level. On day 16, in all test groups the karyocyte counts were higher than in control. Table 8 shows that in all test mice the lymphocyte percentage was higher, and the absolute number of lymphocytes grew faster, than in control throughout the whole observation period. In those mice, who received the peptide more than once, the lymphocytes count in blood at the time of the maximum depletion of the pool of mature cells (on day 4 after the irradiation) was much higher than in control.

This pool, after it goes through cell division and maturation from stem cells to the mature functioning ones, which usually lasts about 8 days, appears in blood. This is observed as an increasing karyocyte count on day 16. Thus, treatment of irradiated mice with the peptide started immediately after the irradiation, i.e. before the bone marrow depleted, led to a greater survival of the remaining hemopoietic progenitors.

Treatment according the scheme did not affect the cellular composition of bone marrow, but it markedly stimulated regeneration of the CFU-S population (FIG. 1). This example illustrates the stimulating effect of intramuscular injections of the peptide of regeneration of the CFU-S population in the bone marrow of irradiated mice (4 Gy).

From each group at least five mice were killed, their bone marrow was taken out and used to prepare the cell suspension, which was injected to lethally irradiated mice. After 9 days, CFU-S was counted in irradiated (4 Gy) donors receiving the peptide by counting the colonies grown on spleen. The results are shown in FIG. 1. It was noted that with intramuscular administration of the peptide the CFU-S count in irradiated mice bone marrow was steadily growing starting from the 4th day, leaving the control CFU-S far behind.

b) According to scheme 2, the peptide injections were made starting from the 3rd day after the irradiation, at the same time of maximum depletion of the pool of mature nucleated cells and the bone marrow. The groups of mice were formed in the same way as in the previous scheme. Blood samples were taken 4 hours after the last injection i.e. on day 6, as well as on days 11, 14, 18, 21. Tables 9 and 10 present the data on karyocyte and lymphocyte counts in blood (per 1 mm$^3$) of mice treated according to scheme 2.

blood from this pool, while the abortive elevation of karyocyte count still lasts in control mice. Throughout the observation period, the contribution of lymphocytes to karyocytes was notably higher in the peptide- treated mice than in control. Absolute lymphocyte count in test mice was higher as compared to control in the period of the abortive elevation (the 6th–11th day after irradiation) and on day 21 in resto-

TABLE 9

| Group | Karyocyte Count in Blood × 10$^3$ on: | | | | | |
|---|---|---|---|---|---|---|
|  | Day 3 | Day 7 | Day 11 | Day 14 | Day 18 | Day 21 |
| (Treatment According to Scheme 2) | | | | | | |
| Control | 1.2 ± 0.1 | 1.38 ± 0.1* | 1.85 ± 0.4* | 2.46 ± 0.3 | 2.33 ± 0.2 | 2.02 ± 0.1 |
| Peptide 1 Time |  | 1.64 ± 0.2 | 1.88 ± 0.3 | 1.50 ± 0.2 | 2.62 ± 0.2 | 1.63 ± 0.2 |
| Peptide 2 Times |  | 1.33 ± 0.2 | 2.03 ± 0.3 | 1.60 ± 0.2 | 1.67 ± 0.1 | 2.70 ± 0.2 |
| Peptide 3 Times |  | 2.22 ± 0.3 | 1.94 ± 0.2 | 1.50 ± 0.2 | 2.07 ± 0.2 | 2.45 ± 0.4 |
| Peptide 4 Times |  | 2.71 ± 0.4* | 3.03 ± 0.5* | 1.17 ± 0.1 | 2.48 ± 0.1 | 1.66 ± 0.2 |

*P < 0.05

TABLE 10

| Group | Lymphocyte in Blood, % (Absolute) on: | | | | | |
|---|---|---|---|---|---|---|
|  | Day 3 | Day 7 | Day 11 | Day 14 | Day 18 | Day 21 |
| (Treatment According to Scheme 2) | | | | | | |
| Control | 24.4 ± 1.7 | 29.0 ± 1.4 (400) | 27.4 ± 1.1 (499) | 29.7 ± 3.2 (731) | 30.9 ± 3.1 (730) | 29.5 ± 3.1 (596) |
| Peptide 1 Time |  | 45.1 ± 3.9 (232) | 49.2 ± 3.8 (1365) | 43.3 ± 3.2 (1118) | 30.6 ± 2.9 (2412) | 45.6 ± 3.9 (743) |
| Peptide 2 Times |  | 52.7 ± 2.9 (701) | 45.1 ± 5.4 (915) | 38.8 ± 2.2 (619) | 42.1 ± 1.4 (703) | 45.2 ± 2.3 (1220) |
| Peptide 3 Times |  | 43.6 ± 2.1 (968) | 46.3 ± 5.4 (892) | 47.7 ± 6.1 (744) | 35.5 ± 1.4 (7353) | 52.5 ± 3.2 (1289) |
| Peptide 4 Times |  | 45.6 ± 2.5 (1231) | 42.6 ± 3.6 (1406) | 44.0 ± 3.1 (515) | 45.1 ± 1.8 (1116) | 47.5 ± 5.3 (789) |

*- p < 0.05

It was shown that karyocyte counts were of the same order in control and test groups throughout the observation period, save those mice who received the peptide 4 times: on days 6 and 11 (the phase of abortive elevation) the number of nucleated cells in them was higher than in control. Interestingly, on day 14 the content of these cells decreased considerably, especially in the group which received 4 peptide injections. Probably, the peptide accelerates maturation of the CFU-S, which survived irradiation, their pool exhausts faster and by the 14th day no mature cells come in ration period. During the second depletion (the 14th–18th day), the lymphocyte counts were equal in test and control groups.

The data in Table 11 reflect the process of bone marrow regeneration in control and test irradiated (4 Gy) mice treated with peptide according to scheme 2. The regeneration was equally intensive in all animal groups till the 11th day, from day 14 to day 18 the nucleated cells counts were considerably higher in the bone marrow of test mice.

TABLE 11

| Group | Karyocyte Count in Femoral Bone Marrow × 10$^6$ on: | | | | | |
|---|---|---|---|---|---|---|
|  | Day 3 | Day 7 | Day 11 | Day 14 | Day 18 | Day 21 |
| (Treatment According to Scheme 2) | | | | | | |
| Control | 9.3 ± 0.8 | 16.8 ± 1.0 | 21.8 ± 1.5 | 13.4 ± 1.9 | 13.7 ± 1.5 | 20.6 ± 0.9 |
| Peptide 1 Time |  | 16.4 ± 0.3 | 17.9 ± 1.8 | 18.7 ± 1.1 | 18.0 ± 0.4 | 22.4 ± 2.2 |
| Peptide 2 Times |  | 14.9 ± 1.7 | 18.6 ± 2.3 | 14.1 ± 1.7 | 17.2 ± 1.0 | 18.9 ± 0.6 |

TABLE 11-continued

| | Karyocyte Count in Femoral Bone Marrow x 10⁶ on: | | | | | |
|---|---|---|---|---|---|---|
| Group | Day 3 | Day 7 | Day 11 | Day 14 | Day 18 | Day 21 |
| Peptide 3 Times | | 12.25 ± 1.3 | 18.5 ± 2.9 | 16.9 ± 0.8 | 16.9 ± 0.8 | 19.5 ± 1.6 |
| Peptide 4 Times | | 2.71 ± 2.7 | 20.3 ± 1.3 | 18.9 ± 0.2 | 17.7 ± 1.2 | 20.0 ± 1.8 |

TABLE 12

| | CFU-S (absolute) in blood on: | | | |
|---|---|---|---|---|
| Group | Day 3 | Day 7 | Day 11 | Day 14 |
| 4 Gy | 297 ± 36.3 | 378 ± 53 | 937 ± 91 | 844 ± 94 |
| N 1 Time | | 459 ± 26 | 858 ± 67 | 1197 ± 75 |
| N 2 Time | | 298 ± 27 | 846 ± 44 | 902 ± 56 |
| N 3 Time | | 305 ± 33 | 1077 ± 56 | 1166 ± 68 |
| N 4 Time | | 431 ± 48 | 1147 ± 55 | 1434 ± 89 |

Figure 2:
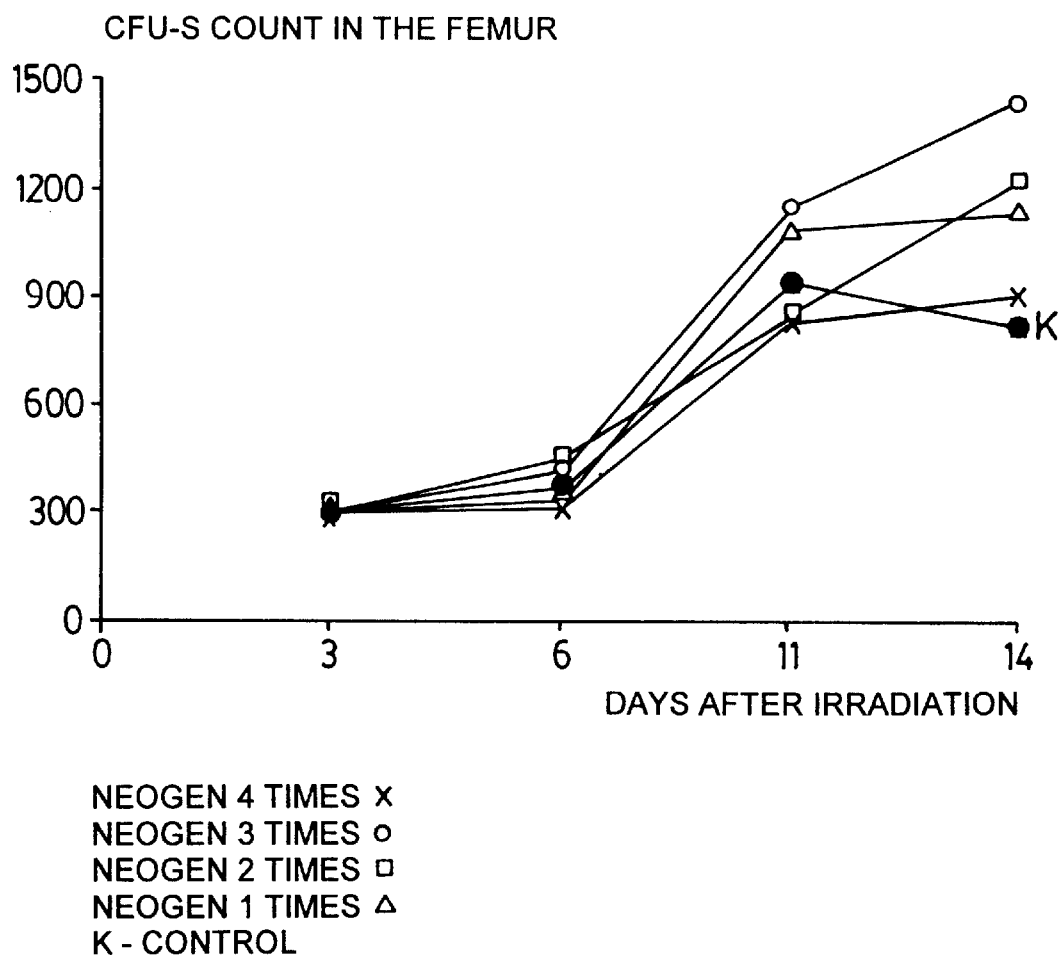
FIG. 2 is a graph which illustrates the effect of intramuscular injections of H-Ile-Glu-Trp-OH on regeneration of the CFU-S population in irradiated mice (4 Gy), wherein the injections are first administered on the 3rd day after irradiation.

Table 12 illustrates that reconsitution of CFU-S Population in Irradiated (4 Gy) and Irradiated (4 Gy) and H-Ile-Glu-Trp-OH (N)-Treated Mice The peptide had a positive effect on the size of the CFU-S population on the 11th day in those mice who received the peptide for 3 or 4 days, and by the 14th day the CFU-S counts in all test groups were greater than in control [see Table 12]. The results are shown in FIG. 2. From day 14 till day 18 a considerable growth of NC count was recorded in the bone marrow of treated mice [see Table 11].

EXAMPLE 8

The effect of the peptide on erythropoiesis in irradiated mice (4 Gy) was also studied. The mice were irradiated and treated with the peptide as in Example 7.

Erythrocyte counts did not differ in test and control groups. In treated mice, hemoglobin level restored faster and become normal by the 11th day, while in control—by day 14. Table 13 presents the results.

TABLE 13

| | Hemoglobin Content (r/dl) in blood on | | | | | |
|---|---|---|---|---|---|---|
| Group | Day 3 | Day 7 | Day 11 | Day 14 | Day 18 | Day 21 |
| | (Treatment According to Scheme 2) | | | | | |
| Control | 7.8 ± 0.9 | 8.4 ± 0.7 | 9.9 ± 0.3 | 12.0 ± 0.4 | 12.1 ± 0.1 | 12.2 ± 0.4 |
| Peptide 1 Time | | 9.4 ± 0.8 | 12.6 ± 0.1 | 11.8 ± 0.5 | 12.1 ± 0.1 | 12.1 ± 0.4 |
| Peptide 2 Times | | 9.6 ± 0.4 | 12.0 ± 0.1 | 10.8 ± 0.8 | 11.5 ± 0.6 | 11.7 ± 0.6 |
| Peptide 3 Times | | 10.15 ± 0.8 | 11.9 ± 0.4 | 12.1 ± 0.2 | 11.7 ± 0.2 | 11.9 ± 0.3 |
| Peptide 4 Times | | 14.4 ± 0.9 | 12.2 ± 0.1 | 12.0 ± 0.2 | 11.7 ± 0.4 | 12.0 ± 0.6 |

The four-injection treatment was most effective in this case.

EXAMPLE 9

In the next series of experiments, the effect of H-Ile-Trp-OH on formation of endogenous spleen colonies in irradiated mice (6 Gy) was studied. The results of the study reflect the response of hemopoietic progenitors to ionising radiation in the body.

Test mice were irradiated in the dose of 6 Gy Beginning from the first hour after the irradiation, the mice received once daily IM injections of 10 μg/kg H-Ile-Glu-Trp-OH. Injections were made 1, 2, 3, or 4 times. The mice were killed on Day 9, spleens were taken out and fixed in Buene's solution, the colonies were counted. 110 mice were used in the test.

TABLE 14

| Group | Colony | P |
|---|---|---|
| 6 Gy | 2.4 ± 03 | |
| N 1 times | 3.3 ± 0.6 | |
| N 2 times | 4.4 ± 0.5 | <0.05 |
| N 3 times | 5.0 ± 0.7 | <0.05 |
| N 4 times | 5.2 ± 0.8 | <0.05 |

The data in the Table 14 show that H-Ile-Glu-Trp-OH significantly increased the yield of endogenous spleen colonies after irradiation with the dose of 6 Gy in all administration schemes except that with one injection. To put it differently, in this experimental system the peptide reduced the destructive effect of ionising radiation on the CFU-S pool.

EXAMPLE 10

The effect of H-Ile-Glu-Trp-OH on hemopoiesis: reconstitution of granulocytes and lymphocytes in cytostatic-treated mice was studied. Also studied was the correcting effect of H-Ile-Glu-Trp-OH in a cytostatic-induced cytopenia of the hemopoietic organs.

Used as a cytostatic, Cytosine-Arabinoside (CA) was intraperitoneally injected to donor mice once in the dose of 20 mg/kg. The peptide was given according to the following scheme: 10 μg/kg once daily, three injections starting from the first hour after CA. Intact mice received H-Ile-Glu-Trp-OH in the same doses and according to the same schedule. On day 8 after the cytostatic injection, determined were karyocyte count in the donor bone marrow and the content of hemopoietic progenitors of different polipotencies: committed CFU-S-8 and CFU-S-12. CFU-8 are committed stem cells which later undergo differentiation. CFU-12 are the polypotent cells, from which stem cells can be recruited (i.e. they maintain the pool of stem cells). This is a slowly proliferating cell population, mainly in G phase. That is why it is important to evaluate the effect of a preparation on the pools of both committed (CFU-8) and polypotent (CFU-12) cells. To this end, bone marrow was extracted from donor's femoral bones and injected to lethally irradiated recipients. After the cell injections, every test group was divided into 2 subgroups: some animals were killed on day 8, the other on day 12. Spleens were taken out and the colonies were counted. The tests were carried out on 105 mice.

TABLE 15

| GROUP | Number of Mice | Karyocytes $\times 10^6$ | Day 8 COUNT CFU-S-8 | CFU-S-12 |
|---|---|---|---|---|
| Control | 24 | 25.0 ± 1.2 | 2674 ± 150 | 2841 ± 188 |
| Control + N | 20 | 23.0 ± 0.9 | 2805 ± 232 | 2930 ± 152 |
| CA | 24 | 17.5 ± 0.8* | 1270 ± 53* | 1244 ± 71* |
| CA + N | 24 | 22.0 ± 0.7 | 1644 ± 154 | 2488 ± 203 |

*- Significance was calculated relative to this group
$P < 0.05$

The result of the effect of H-Ile-Glu-Trp-OH on reconstitution of CFU-S-8 and CFU-S-12 and karyocyte count after cytostatic treatment are shown in Table 15. The cytostatic CA lowered the karyocyte count in the bone marrow and halved CFU-S-8 and CFU-S-12 counts as compared to control. With the H-Ile-Glu-Trp-OH therapy, by day 8 the karyocyte count had been completely reconstituted, the CFU-S-8 population had grown significantly, the CFU-S-12 pool had reached the values of the intact control. Noteworthy is that H-Ile-Glu-Trp-OH most effectively reconstituted the compartment of polipotent progenitors (CFU-S-12) able to originate not only all lines of hemopoiesis but also immune cells.

So, H-Ile-Glu-Trp-OH was found to help restore hemopoiesis after exposure to such factors as ionising radiation and cytostatics.

EXAMPLE 11

The influence of the oxyurea on the tumor cells, treated by synthetic H-Ile-Glu-Trp-OH was studied.

Various cytostatics (preparations which stop the proliferation of cells) are included in the traditional schemes of treatment of any malignant tumors. One of them is the oxyurea (OU).

The goal of this series of experiments was to examine the response of the thymoma EL-4 cells to action of OU after their incubation with H-Ile-Glu-Trp-OH.

The Thymoma EL-4 cells were extracted from the abdomen cavity of C57B1 mice at the 7th day after transplantation. The suspension was washed by centrifugation in the medium RPMI. Then the cells were resuspended in the growth medium (RPMI+10% of embryo serum+0.1% penicillin/streptomycin) and were split in culture flasks 5 ml each (10 ml cells per flask). 2 mg of the preparation were added (20 µl) to each probe. After 18 hours of incubation (37 degrees Celsius $CO_2$), OU was added to the half of probes (1 mg per 5 ml). Incubation was done for 1 more hour in the same conditions and then cells were washed out by centrifugation in the medium RPMI. The precipitated cells were resuspended in calculation 1 ml per 0.2 ml of RPMI medium and then transplanted to the mice C57B1 under the back skin.

The taking of the measurements of the size of the tumor was started after the knot became visible. The tumor was measured every day until it was impossible to measure. The survival ability of the mice was examined during 60 days after transplantation. Mice that survived after this period were considered to be cured. Each experimental group consisted of 6 animals.

Figure 3A:
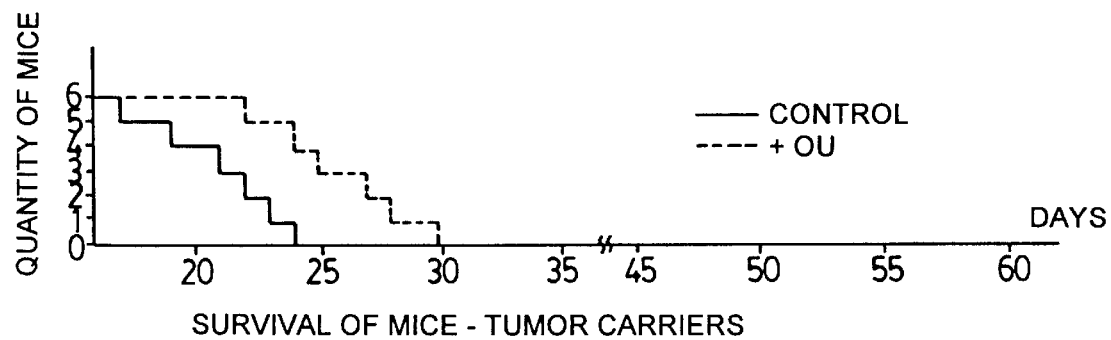
FIG. 3 is a graph illustrating the survival of mice with tumors (Thyoma EL-4 cells) after treatment with oxyurea (OU) [FIG. 3a] and oxyurea and H-Ile-Glu-Trp-OH [FIG. 3b].
Figure 3B:
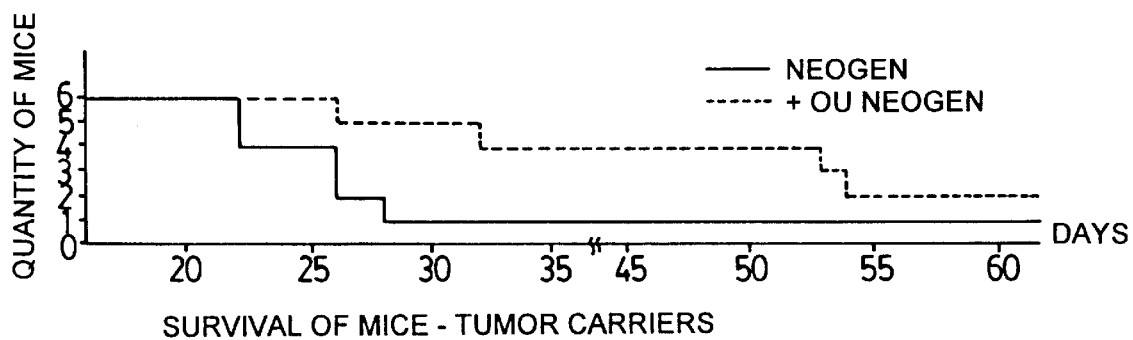

The treatment of the intact tumor cells (control) with OU causes approximately a 12-day delay in the tumor growth (FIG. 3). During the action of cytostatics on the thymoma cells, incubated with H-Ile-Glu-Trp-OH, the depression of the tumor growth on the 12th day is most definite (the dimensions of the tumor are smaller than those of the group not treated with OU).

The incubation of thymoma EL-4 cells with any of the tested peptides caused some delay in growth of the tumor (registered in mm squared) in comparison with the control. This effect was more definite before the 10th day of growth, then the rate of the tumor growth was comparable with control.

The results of the survival experiments on mice are shown in FIG. 3 and Table 16.

TABLE 16

Influence of Immunomodulators on the Survival and Average Lifespan of Mice with Thymomo EL-4

| Group | Number of Survived Mice From 6 | % of Survival | Average of Lifetime |
|---|---|---|---|
| Control | 0/6 | 0 | 21.0–± 1.3 |
| Control + OU | 0/6 | 0 | 26.0–± 1.1 |
| H-Ile-Glu-Trp-OH | 1/6 | 16.6 | 24.5–± 1.0 |
| H-Ile-Glu-Trp-OH + OU | 2/6 | 33.3 | 41.2–± 16.0 |

The result in Table 16 and FIG. 3 show the increase in lifetime of 5 days of mice with tumor, treated by OU.

Incubation of the tumor cells with H-Ile-Glu-Trp-OH extended the lifetime of animals by 4 days and in combination with cytostatics by 15 days. On average the lifetime of the animals treated by H-Ile-Glu-Trp-OH and OU was 20 days longer than the control group. Only in these groups were surviving animals registered after 60 days.

Therefore, a positive effect on the dynamic of growth of tumor (delay) and the lifetime extension of the experimental animals was found by incubation of the Thymoma cells with synthetic immunomodulators. Immunostimulants (H-Ile-Glu-Trp-OH) can potentiate the damaging action of cytostatic on the Thymoma cells.

EXAMPLE 12

At the present time hyperthermia is widely used in the treatment of malignant tumors, and not only locally, but during autologic transplantation of the bone marrow for the therapy of leukosis (when it is not possible to find an identical donor). The influence of H-Ile-Glu-Trp-OH on the growth of tumor cells EL-4, treated by hyperthermia, was examined.

Incubation of the tumor cells with the tested drugs were performed the same way as described above in the experiments with OU. After 18-hour incubation, the cells were washed in the medium RPMI, and then resuspended in the concentration of 5 ml/1 ml in plastic test tubes of total volume of 2 ml each. Then the cells were heated for 1 hour at 43 degrees Celsius, and transplanted under the back skin of the mice C57B1. The growth of the tumor was examined the same way as described above.

TABLE 17

Influence of Heating and H-Ile-Glu-Trp-OH on Tumor Size - EL-4 (13th day)

| Group | Number Of Mice | Tumor size in mm squared |
| --- | --- | --- |
| Control | 6 | 230.1 |
| Control + Heating | 6 | 10.8 |
| H-Ile-Glu-Trp-OH | 6 | 188.7 |
| H-Ile-Glu-Trp-OH + Heating | 6 | No Tumor |

The results indicated that after heating of the intact Thymoma EL-4 cells and preliminary treatment in vitro with H-Ile-Glu-Trp-OH, followed by heating on the 21st day, no tumor formation was observed in any of the mice in that group. The mice were observed for 25 days.

EXAMPLE 13

Action of H-Ile-Glu-Trp-OH on the proliferation of a mixed lymphocyte culture (MLC) was studied.

This experimental system is an in vitro the analog of the Graft Versus Host Disease reaction.

In the present series of experiments the reaction H-2d, anti H-2b was examined. The new combination responder-stimulator. Each variant was made in a triplet. Microcultures were incubated for 4 days, then 3H-thymidine was added; then the mixture was incubated for 16 more hours, and after its transfer to the filters, the amount of 3H-thymidine was determined. H-Ile-Glu-Trp-OH was added at the beginning of the incubation in different concentrations. The results are presented as indexes of stimulation of proliferation.

Figure 4:
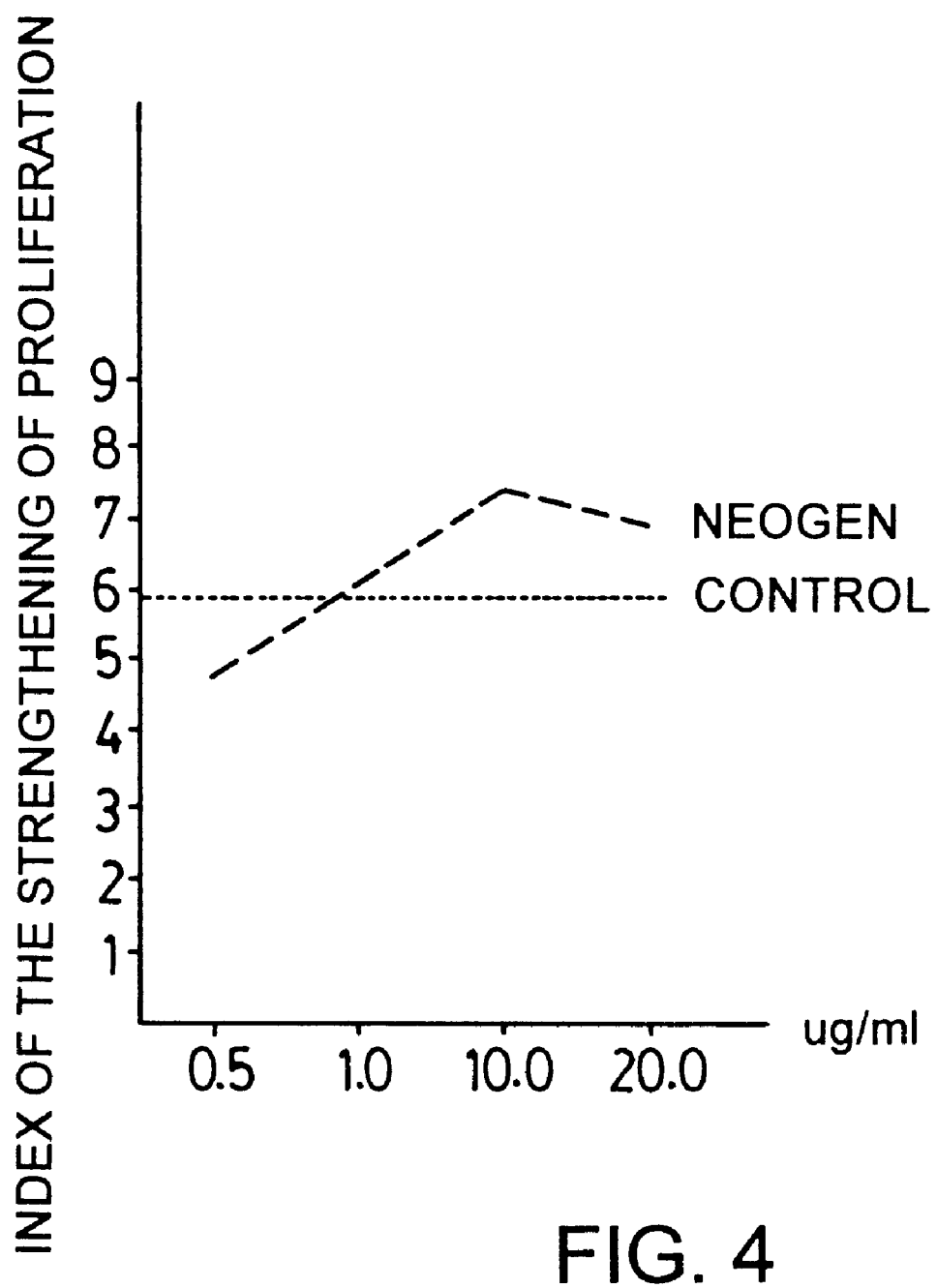
FIG. 4 is a graph illustrating the index of stimulation of proliferation of mixed lymphocyte cultures treated with H-Ile-Glu-Trp-OH.

The results are presented in FIG. 4. The results show that H-Ile-Glu-Trp-OH in concentrations 1, 10, and 20 $\mu$g/ml produces stimulation of proliferation of the allogenic lymphocytes, while in concentrations of 0.1 $\mu$g/ml it exhibited negligible inhibition of the proliferation.

EXAMPLE 14

The use of H-Ile-Glu-Trp-OH in treatment of patients with hemopoietic diseases was studied.

The clinical study of H-Ile-Glu-Trp-OH was continued in groups of patients with pronounced secondary pathological changes in their immune system. The primary task of the first stage of the investigation was to observe the preparation tolerance, to reveal toxic, allergic and other reactions, hemogram dynamics and biochemical indices. Further investigation, along with further monitoring of the major clinical and laboratory parameters, included evaluation of the immunological status of a patient before and after the immunopeptide treatment.

The effect of the immunopeptides on hemopoietic status was assessed on the basis of the dynamics of a number of immunological tests characterising both humoral and cellular immunity.

Materials And Methods

The study was continued in groups of patients with immune cytopenias, multiple myeloma, chronic lymphoid leukosis, lymphocytic lymphomas, lymphosarcomas (55 patients). Special attention was paid to the group of patients with P-cellular lymphoid leukosis. The peculiarity of the leukemic B-lymphocyte clone and its relatively vast representation in the peripheral blood of patients with a pronounced secondary immune deficiency makes B-cellular chronic Lymphoid leukosis a unique model for clinical studies of the effect of an immunomodulator.

Research Methods

Immune phenotyping is the most reliable method to determine the changes of ratios of immunocompetent cells in the peripheral blood and lymphocyte-containing organs. The method allows detection of subpopulations by the presence of cellular differentiating antigen structures on lymphocyte surface. For more trustworthy results, some patients were examined using a flow-type cytoflourimeter and monoclonal antibodies. Taking into account the contingent of the patients, the main surface structures to be examined were the following: CD45++CD14–, CD45+CD14–, CD45+CD14+, CD3+CD19–, CD3–CD19+, CD4+CD8–, CD4–CD8+, CD3+HLA– DR+, CD3+CD16,56+, CD34+, CDS+.

The dynamics of CD4+CD8– and CD4–CD8+ (T-helpers and T-suppressers) and the dynamics of other necessary CD-markers were determined in the course of treatment with H-Ile-Glu-Trp-OH. A special attention was paid to CD45++ CD14– and CD45+CD14 as they characterize the proportion between normal and leukemic lymphocytes in chronic lymphoid leukosis and illustrate the influence of the immunoactive peptide on the proportion. These peculiarities connected with the characteristics of the disease allow investigation of the molecular mechanism of its genesis. In the case of an immune cytopenia most important are the quantitative ratios of CD45++CD14– and CD45+CD14– to CD4–CD8+, their reliable values can be obtained with the help of a cytofluorimeter.

The other clinical and instrumentally methods of investigation and observation remained the same as earlier:

Before instituting the treatment, examination was carried out including case history, clinical, laboratory and instrumental investigations. Necessary morphological investigations were performed to verify the diagnosis. There were also the results of hemogram dynamics before and after each treatment course of H-Ile-Glu-Trp-OH. After these courses the biochemical indices and urine tests were examined again. X-ray, ultrasonic and morphological examinations were repeated on indication.

The incidence rate of infectious inflammatory diseases in patients treated with H-Ile-Glu-Trp-OH was further recorded.

For patients on cytostatic therapy, the following were recorded: the date of the beginning of a next course, the necessity to prolong the interval between courses in connection with unsatisfactory hemogram indices, as well as the cases of dosage adjustments.

Humoral immunity was also investigated: the content of different types of immunoglobulins, protein fractions, antibodies to thyroid, and the Coombs test (the latter was performed in the case of haemolytic anaemia).

H-Ile-Glu-Trp-OH Treatment Protocol

One ml daily, intranasally, once or twice in divided doses, for 5 days. The course was repeated after a 3-week interval. To those patients who received a cytostatic mono- or polychemotherapy, H-Ile-Glu-Trp-OH was administered from the first day of the break in the cytostatic treatment.

Treatment Results-H-Ile-Glu-Trp-OH

In the period of a prolonged administration of H-Ile-Glu-Trp-OH (5–6 courses) no complaints of the patients were noted. There were no toxic reactions, skin rash, disturbances of gastrointestinal function, central or peripheral nervous system, vascular, muscular or other adverse reactions.

Physical investigations of patients before and after the treatment revealed no such changes of the somatic status, which could be ascribed to the action of the test preparation.

The dynamics of biochemical indices—bilirubin, alanine and asparaginic transaminases, alkaline phosphatase, lactate dehydrogenase, glucose, carbamide, creatinine, uric acid, total protein, protein fractions, electrolytes—before and after 1–3 treatment courses revealed no changes associated with H-Ile-Glu-Trp-OH administration. We failed to reveal any changes in AP dynamics and ECG caused by H-Ile-Glu-Trp-OH. Noteworthy is that we observed no toxic manifestations, deviations of biochemical indices, or shifts on the part of the cardiovascular system not only after the first course but also after a series of H-Ile-Glu-Trp-OH courses. For this reason, these indices are not presented in detail for each group.

Examination of hemograms for a longer observation period showed little difference from the results presented in the previous report. APcer treatment with H-Ile-Glu-Trp-OH,the same positive dynamics was noted as in the case of its administration to patients with depression of granulocytic cell line.

Humoral status was evaluated—detection of protein fractions and immunoglobulins in patients' sera. No dynamics of these indices was found. It should be mentioned that the repeated detection of protein fractions and serum immunoglobulins was performed 1–1.5 months after the treatment, because in that period there was a probability of immunopeptidedependent stimulation of immunoglobulin production.

Cellular immunity studies showed the most conspicuous results in patients with chronic lymphoid leukosis. Below are cited the examples of indices dynamics in patients who did not receive steroid and cytostatic therapy before (at least 6 months) and during treatment with H-Ile-Glu-Trp-OH.

Patient M., born in 1925. Chronic lymphoid leukosis since 1990 Treatment: COPP—6 courses, M-2–6 courses with Thymogen after the courses till 1995 with positive effect. No further treatment with cytostatics. Since October 1996—has been receiving H-Ile-Glu-Trp-OH. The dynamics of indices before and after H-Ile-Glu-Trp-OH treatment course: leukocytes 7.9–8.6 blnA, Lymphocytes 41–42% (3.24–3.62 bln/1).

TABLE 18

| Cell Phenotype Subpopulation | % of Cells, Normal | % of Cells, Test Sample | Absolute Count, bln/l | % of Cells after H-Ile-Glu-Trp-OH Treatment | Absolute Count, bln/l |
|---|---|---|---|---|---|
| CD45++CD14– lymphocytes | | 28.7 | 2.27 | 43.2 | 3.715 |
| CD45+CD14– granulocytes | | 60.0 | | 47.7 | |
| CD45+CD14+ monocytes | | 4.5 | | 4.5 | |
| CD3+CD19– T-lymphocytes | 58.2–84.3 | 41.9 | | 35.6 | |
| CD3–CD19+ B-lymphocytes | 7.1–23.3 | 59.0 | | 61.2 | |
| CD4+CD8– T-helpers | 31.4–63.8 | 15.8 | | 11.6 | |
| CD4–CD8+ T-suppressers | 18.9–47.9 | 32.9 | | 30.6 | |
| CD4+/CD8+ ratio | 0.6–3.0 | 0.5 | | 0.4 | |
| CD3+HLA-DR+ activated T-lymphoc. | 3.5–25.9 | 7.4 | | | |
| CD3–CD16,56+ Nat. Killers | 5.4–33.5 | 11.6 | | | |
| CD34+ stem cells | | 0.4 | | | |
| CD5+ T-cell. marker | | 95.5 | | | |

According to the presented data (patient M.), before the beginning of the treatment course the lymphocyte count found by surface markers did not correspond to that obtained in the stained smear. At the same time, the total count of B- and T-lymphocytes (CD3+CD19 and CD3–CD19+) was in line with the number of cells having the CD5+ marker. It shows that CD5+ markers are carried not only by T-lymphocytes, but also by B-lymphocytes, which, as a rule, occurs in B-cellular chronic lymphoid leukosis. Thus, a complete clinical and haematological remission was not observed in the patient. After the course of H-Ile-Glu-Trp-OH the number of CD45++CD14--lymphocytes (supposedly, non-leukaemia) in blood grew significantly, while the relative and absolute lymphocyte counts determined morphologically and in smears of peripheral blood were the same. The ratio of CD4+CD8− and CD4−CD8+ (helpers and suppressers) remained as before.

Patient S., born in 1926. Chronic lymphoid leukosis since 1985. Was not treated with cytostatics. Since October 1996—has been receiving monthly courses of H-Ile-Glu-Trp-OH. The dynamics of indices before and after the H-Ile-Glu-Trp-OH treatment course: leukocytes 57.2–67.5 bin/1, lymphocytes 84–86% (48.04–58.06 bln/1).

cytes were. The diagnosis of B-cellular lymphoid leukosis was not doubted since most of the B-lymphocytes carry the CD5+ marker. After the treatment with H-Ile-Glu-Trp-OH, the count of lymphocytes belonging to the population of conventionally normal lymphocytes doubled. The ratio of CD4+CD8− and CD4−CD8+ (helpers and suppressers) had a tendency to normalisation and overcoming of the predominance of suppressers characteristic of B-cellular lymphoid leukosis.

TABLE 19

| Cell Phenotype Subpopulation | % of Cells, Normal | % of Cells, Test Sample | Absolute Count, bln/l | % of Cells after H-Ile-Glu-Trp-OH Treatment | Absolute Count, bln/l |
|---|---|---|---|---|---|
| CD45++CD14− lymphocytes | | 5.9 | 3.37 | 13.5 | 9.112 |
| CD45+CD14− granulocytes | | 83.7 | | 78.0 | |
| CD45+CD14+ monocytes | | 0.7 | | 0.8 | |
| CD3+CD19− T-lymphocytes | 62.8–85.0 | 61.3<br>1.7* | | 52.0<br>2.6* | |
| CD3−CD19+ B-lymphocytes | 7.1–23.3 | 15.8<br>90.9* | | 40.0<br>96.9* | |
| CD4+CD8− T-helpers | 31.4–63.8 | 22.1<br>1.4* | | 27.1<br>1.6* | |
| CD4−CD8+ T-suppressers | 18.9–47.9 | 44.8<br>0.7* | | 36.5<br>1.9* | |
| CD4+/CD8+ ratio | 0.7–3.3 | 0.5<br>2.0* | | 0.7<br>0.5* | |
| CD3+HLA-DR+ activated T-lymphoc. | 2.8–17.3 | 4.2<br>0.2* | | 16.0<br>0.5* | |
| CD3−CD16,56+ Nat. Killers | 4.8–26.7 | 16.0<br>0.3* | | | |
| CD34+ stem cells | | 0.1 | | | |
| CD5+ T-cell. marker | | 78.9<br>78.9* | | | |

*% of cells in the CD45+CD14− subpopulation (leukemic lymphocytes and granulocytes, the latter being in small quantities in chronic lymphoid leukosis)

The data in Table 19 show a discrepancy between the morphologically obtained typical pattern of lymphoid leukosis and the small lymphocyte count by the CD45++CD14 fraction. For clarity, we presented ratios in the CD45+ CD14− fraction, where the majority of leukaemia lympho- Patient 0., born in 1929. Chronic lymphoid leukosis since 1996. Was not treated with cytostatics. H-Ile-Glu-Trp-OH treatment—since Feburary 1997. The dynamics of indices before and after the treatment course: leukocytes 17.3–20.8 blnd, Lymphocytes 65–74%(11.2–15.4 blnd).

TABLE 20

| Cell Phenotype Subpopulation | % of Cells, Normal | % of Cells, Test Sample | Absolute Count, bln/l | % of Cells after H-Ile-Glu-Trp-OH Treatment | Absolute Count, bln/l |
|---|---|---|---|---|---|
| CD45++CD14− lymphocytes | | 9.1 | 1.54 | 28 | 5.8 |
| CD45+CD14− granulocytes | | 83.3 | | 63.8 | |
| CD45+CD14+ monocytes | | 2.5 | | 3.6 | |
| CD3+CD19− T-lymphocytes | 58.2–84.3 | 6.9* | | | |
| CD3−CD19+ B-lymphocytes | 7.1–23.3 | 88.8* | | | |
| CD4+CD8− T-helpers | 31.4–63.8 | 3.5* | | 8.2* | |
| CD4−CD8+ T-suppressers | 18.9–47.9 | 5.2* | | 8.1* | |
| CD4+/CD8+ | 0.6–3.0 | 0.7* | | 1.0* | |

TABLE 20-continued

| Cell Phenotype Subpopulation | % of Cells, Normal | % of Cells, Test Sample | Absolute Count, bln/l | % of Cells after H-Ile-Glu-Trp-OH Treatment | Absolute Count, bln/l |
|---|---|---|---|---|---|
| ratio | | | | | |
| CD3+HLA-DR+ activated T-lymphoc. | 3.5–25.9 | 1.0* | | | |
| CD3–CD16,56+ Nat. Killers | 5.4–33.5 | 3.7* | | | |
| CD34+ stem cells | | —* | | | |
| CD5+ T-cell. marker | | 95.0* | | | |

*% of cells in mixed population of CD45++CD14– and CD45+CD14– (we failed to isolate the population of normal lymphocytes).

The data in Table 21, as in the previous cases, show the lymphocyte predominance in peripheral blood smears and their small quantity in the CD45++CD14– fraction, which is common to B-cellular chronic lymphoid leukosis. This fraction is a graphic example of the growth of cells with CD45++CD14– markers after treatment with H-Ile-Glu-Trp-OH-1: their number grew three times. An increase and normalisation of helper/suppresser ratio was also noted.

Patient B., born in 1926. Chronic lymphoid leukosis since 1984. Did not receive cytostatics during the treatment. The dynamics of indices before and after treatment with H-Ile-Glu-Trp-OH: leukocytes 23,0–26.6 bln/1, Lymphocytes 85–82% (18.7–21.8 bln/1).

distinct tendency towards increase of CD45++CD14– cells characteristic of normal lymphocytes. At the same time, there was a relative decrease in the number of cells in the CD45+CD14– fraction, the majority of which are leukaemia lymphocytes.

The findings suggest that H-Ile-Glu-Trp-OH helps increase the lymphocyte fraction with the markers, which allow assigning them to healthy cells CD45++CD14–. Besides, there is a tendency to an increase and normalisation of the T-helper/T-suppresser ratio.

EXAMPLE 15

To establish the safety of use of the peptides, toxicity tests were performed. Toxicity tests where performed in accor-

TABLE 22

| Cell Phenotype Subpopulation | % of Cells, Normal | % of Cells, Test Sample | Absolute Count, bln/l | % of Cells after H-Ile-Glu-Trp-OH Treatment | Absolute Count, bln/l |
|---|---|---|---|---|---|
| CD45++CD14– lymphocytes | | 11.3 | 2.5 | 9.5 | 2.52 |
| CD45+CD14– granulocytes | | 82.7 | | 86.4 | |
| CD45+CD14+ monocytes | | 1.8 | | 2.1 | |
| CD3+CD19– T-lymphocytes | 62.8–85.0 | 8.0* | | 10.6* | |
| CD3–CD19+ B-lymphocytes | 7.1–23.3 | 89.0* | | 85.3* | |
| CD4+CD8– T-helpers | 31.4–63.8 | 5.9* | | 6.4* | |
| CD4–CD8+ T-suppressers | 18.9–47.9 | 4.4* | | 3.8* | |
| CD4+/CD8+ ratio | 0.7–3.3 | 1.3* | | 1.7* | |
| CD3+HLA-DR+ activated T-lymphoc. | 2.8–17.3 | 1.5* | | 1.31* | |
| CD3–CD16,56+ Nat. Killers | 4.8–26.7 | 2.5* | | | |
| CD34+ stem cells | | 0* | | | |
| CD5+ T-cell. marker | | 93.1* | | | |

In this case, there was also a discrepancy between the lymphocyte number found in the morphological examination and that in the CD45++CD14– fraction. After the treatment the ratio improved significantly.

In those cases when patients with chronic lymphoid leukosis were treated with H-Ile-Glu-Trp-OH, there was a dance Pharmacological Committee Russian Federation (RF) "guidelines for the pre-clinical study of general toxic activity of new pharmacological compounds". M., 1985.

I. Acute Toxicity

Acute toxicity was studied in 120 mice (60 males, 60 females). Ld$_{50}$ was not reached with the dose 10000 times as high as the therapeutic one. The preferred therapeutic dose is 0.001–0.1 mg/kg.

Acute toxicity was studied in 20 guinea pigs and 6 dogs. No toxic effects were observed. The drug has a wide therapeutic range.

II. Chronic Toxicity

The pathomorphologic investigation of animals (with histologic investigation of organs) failed to find any pathologic processes in the subject animals.

II.1 The H-Ile-Glu-Trp-OH effect on the composition and properties of the peritheric blood, the morphological state of the internals.

The drug was injected once daily for 30 days.

The test animals were 20 rabbits and 40 guinea pigs. The results of the test showed that H-Ile-Glu-Trp-OH did not cause any pathologic changes in the body or peritheric blood.

II.2 The effect of H-Ile-Glu-Trp-OH on the cardio-vascular and respiratory systems.

The effects of H-Ile-Glu-Trp-OH on ECG and arterial pressure were studied in guinea pigs and cats.

The test was conducted in 20 guinea pigs.

The influence of H-Ile-Glu-Trp-OH on arterial pressure was studied in 10 cats. No significant difference from control was found both in ECG readings and arterial pressure. Therefore, the drug did not cause any disorders in functioning of the cardio-vascular or respiratory systems.

II.3. The effect of H-Ile-Glu-Trp-OH on liver function.

The tests were performed in 20 rabbits, who received injections of 0.01% H-Ile-Glu-Trp-OH solution for 30 days. H-Ile-Glu-Trp-OH was shown not to have any toxic effect on the liver function.

II.4. The effect of H-Ile-Glu-Trp-OH on kidney function

The anti-diuretic activity of H-Ile-Glu-Trp-OH was studied in 40 white mice. H-Ile-Glu-Trp-OH was shown not to have any anti-diuretic activity.

II.4. Local irritating effect of H-Ile-Glu-Trp-OH

The local irritating effect of H-Ile-Glu-Trp-OH was studied in 20 guinea pigs and 5 rabbits. H-Ile-Glu-Trp-OH was shown to have no local irritating effect.

II.5. Allergenicity study of H-Ile-Glu-Trp-OH

The study was performed in 12 rabbits, who received subcutaneous injections of 0.01% H-Ile-Glu-Trp-OH solution for 5 days. The control animals were injected with horse serum. No macroscopic reaction was observed on the H-Ile-Glu-Trp-OH injection sites.

In the chronic toxicity study, no side effects were observed with the doses 10–100 times as large as the therapeutic ones. The general state of the animals, behaviour, motor function, cardio-vascular, respiratory activity, liver and kidney functions were within the range of physiologic fluctuations.

The pathomorphologic investigation of animals (with histologic investigation of organs) failed to find any pathologic processes in the body.

The absence of side effects from H-Ile-Glu-Trp-OH administration in animals makes it possible to recommend the drug for clinical testing.

III. This example describes the toxicity study of the peptide.

To determine the peptide toxicity, male mice received single injections of the peptide in the dose of 0.15 g per kg body weight, which was 15,000 times as large as the therapeutic dose with favourable effect in post-irradiation regeneration of hemopoietic progenitors. The second group of mice received daily peptide injections in the dose of 10 $\mu$g/kg (the therapeutical dose) for 5 days. Survival of the animals was observed for 30 days. Not an animal died in the first group or in the second one. On the 14-th day after the peptide injection 10 mice from each group were killed to determine the condition of their cellular systems. Nucleated cells were counted in spleen and thymus (per mg of organ weight), bone marrow, blood (per ml). Erythrocyte count and hemoglobin level were determined. The results are presented in tables 22 and 23.

TABLE 22

| | | karyocyte count | | |
|---|---|---|---|---|
| group | weight | spleen ($10^3$/mg) | thymus ($10^3$/mg) | bone marrow × $10^7$/femur |
| control | 21–22.5 | 1100 ± 90* | 1850 ± 260** | 2.1 ± 0.18 |
| peptide (0.15 g/kg) | 21–22.0 | 2280 ± 30* | 3030 ± 250** | 2.39 ± 0.25 |
| peptide (10 mcg/kg) × 5 injections) | 21–22.5 | 1760 ± 100 | 2780 ± 340 | 1.94 ± 0.2 |

*, **= statistically reliable

TABLE 23

| group | karyocytes ($10^3$) | karyocytes %/absolute | erythrocyte ($10^3$) | hemoglobin g/dl |
|---|---|---|---|---|
| control | 7.1 ± 0.9 | 57.4 ± 2.8 4075 | 8600 ± 500 | 11.8 ± 0.3 |
| peptide (0.15 g/kg) | 5.4 ± 0.7 | 62.0 ± 3.4 3348 | 8100 ± 600 | 10.8 ± 0.7 |
| peptide (10 mcg/kg × 5 injections) | 10.1 ± 0.8 | 58.6 ± 3.6 | 8400 ± 200 | 11.5 ± 0.2 | as the data show, 14 days after the injection of the large single dose of the peptide the karyocyte count in spleen and thymus went up. Five injections of the therapeutical dose caused by trustworthy elevation of nucleated cells count in thymus per mg thymus. The rest of determined indices in both test groups did not differ from control. Thus, the peptide dose as large as 15,000 times the therapeutic dose did not cause death of mice or toxic effects as regards the cells of blood, spleen, thymus, bone marrow. The same is also true for long (for 5 days) peptide adminstration. It should be mentioned that throughout the experiment no weight losses were recorded in mice. Moreover, their average weight grew by 2 g by the end of the study, the same as in control.

Thus, $LD_{50}$ of the peptide was not found, since even doses 15,000 as large as the therapeutical one neither killed mice, nor produced any side effects.

Noteworthy is that no toxic or allergic reactions were observed either during the study of the H-Ile-Glu-Trp-OH specific and general pharmacological activity or during the 1–6 month observation period after the study.

The study of the specific and general pharmacological activity of H-Ile-Glu-Trp-OH showed H-Ile-Glu-Trp-OH to have a pronounced stimulating effect on cellular and humoral immune response and non-specific resistance of the organism.

In the study of specific and general pharmacological activity, the test animals were mice, guinea pigs, rats, rabbits. Some tests were performed using lymphocyte or monocyte cultures of the peritheric blood of donors and patients with different diseases accompanied by immunity disorders.

H-Ile-Glu-Trp-OH may be recommended for clinical tests in patients with different immunodeficiency states as a means of normalisation of the immunologic reactivity of the organism. H-Ile-Glu-Trp-OH parenteral (intramuscular or subcutaneous) doses of preferably, 0.001–0.01 mg/kg produce a marked immunoregulatory effect when administered, preferably, daily for, preferably, 3–10 days.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

What is claimed is:

1. A method of modulating hemopoiesis in an animal comprising administering to the animal an effective amount of one or more of the peptides of formula I:

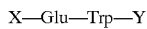
X—Glu—Trp—Y  (I)

wherein X is H, Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, His, Lys, Arg γ-aminobutyric acid, or ξ-aminocaproic acid; Y is Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, Arg, γ-aminobutyric acid, ξ-aminocaproic acid, —OH, $NH_2$, $N_2H_3$, or a mono- or di-substituted amide ($C_1$–$C_3$); with the proviso that when X is H, Y is not —OH and a pharmaceutically acceptable carrier.

2. The method of modulating hemopoiesis in an animal according to claim 1 wherein the one or more peptides are selected from the group consisting of: H-Ile-Glu-Trp-OH, His-Glu-Trp-OH, H-Glu-Trp-$NH_2$, H-Glu-Trp-Arg, Lys-Glu-Trp-OH, Arg-Glu-Trp-OH, H-Glu-Trp-Tyr, Lys-Glu-Trp-Tyr, H-Glu-Trp-$N_2H_3$, H-Glu-Trp-Gly, and Val-Glu-Trp-OH.

3. The method of modulating hemopoiesis in an animal according to claim 2 wherein the one or more peptides comprises H-Ile-Glu-Trp-OH.

4. The method of modulating hemopoieses in an animal according to claim 3 wherein the one or more peptides consists of H-Ile-Glu-Trp-OH.

5. The method according to claim 1 wherein an effective amount of the peptide is 0.001–0.1 mg/kg weight of the animal.

6. The method according to claim 1 wherein the modulation of hemopoiesis comprises stimulating hemopoieses in an animal.

7. The method of claim 6 wherein the one or more peptides comprises H-Ile-Glu-Trp-OH.

8. The method according to claim 1 wherein the modulation of hemopoiesis comprises the restoring of hemopoiesis in an animal with impaired hemopoiesis.

9. The method according to claim 7 wherein the one or more peptides comprises H-Ile-Glu-Trp-OH.

* * * * *